United States Patent
Hicks et al.

(10) Patent No.: US 11,471,076 B2
(45) Date of Patent: Oct. 18, 2022

(54) DEVICE AND KIT FOR INDICATING A PH AT A LOCUS

(71) Applicants: Smith & Nephew PLC, Watford (GB); University of Sheffield, Sheffield (GB)

(72) Inventors: John Kenneth Hicks, York (GB); Richard Hoskins, Bradford (GB); Stephen Rimmer, Bradford (GB); Dorothy McCulloch, York (GB)

(73) Assignees: Smith & Nephew PLC, Watford (GB); University of Sheffield, Sheffield (GB)

( * ) Notice: Subject to any disclaimer, the term of this patent is extended or adjusted under 35 U.S.C. 154(b) by 1014 days.

(21) Appl. No.: 16/070,260

(22) PCT Filed: Jan. 13, 2017

(86) PCT No.: PCT/EP2017/050704
§ 371 (c)(1),
(2) Date: Jul. 13, 2018

(87) PCT Pub. No.: WO2017/121871
PCT Pub. Date: Jul. 20, 2017

(65) Prior Publication Data
US 2019/0008428 A1 Jan. 10, 2019

(30) Foreign Application Priority Data

Jan. 14, 2016 (GB) .................................... 1600747

(51) Int. Cl.
*A61F 13/00* (2006.01)
*A61B 5/00* (2006.01)
(Continued)

(52) U.S. Cl.
CPC .......... *A61B 5/14539* (2013.01); *A61B 5/445* (2013.01); *A61F 13/00055* (2013.01);
(Continued)

(58) Field of Classification Search
CPC .... A61F 2013/0071; A61F 2013/00719; A61F 2013/00948; A61F 2013/00965;
(Continued)

(56) References Cited

U.S. PATENT DOCUMENTS 2,249,867 A 7/1941 Snelling
3,596,657 A 8/1971 Eidus
(Continued)

FOREIGN PATENT DOCUMENTS

AU 2003204827 5/2006
CN 100484501 5/2009
(Continued)

OTHER PUBLICATIONS

Dargaville et al., Sensors and imaging for wound healing: A review, Biosensors and Bioelectronics, vol. 41(2013), pp. 30-42 (Year: 2013).*

(Continued)

*Primary Examiner* — Jacqueline Cheng
*Assistant Examiner* — Tho Q Tran
(74) *Attorney, Agent, or Firm* — Knobbe, Martens, Olson & Bear, LLP

(57) ABSTRACT

Device comprising polyurethane material for indicating pH at a locus, preferably as indication of presence of microbes, comprising a polyurethane network having immobilised therein one or more hydrophilic copolymers, the or each said copolymer comprising:
hydrophilic monomer; and
indicator monomer, which provides an indication in response to a change in hydrophilic state of said hydrophilic monomer and/or copolymer;
characterised in that the or each copolymer further comprises one or a plurality of ionisable groups or moieties or polymerisable monomers having one or more characteristic (Continued)

pKa values in the range 5 to 10 and which are responsive to pH at the locus in the range pH 5 to pH 10 and in that hydrophilic state of hydrophilic copolymer is dependent on ionisation of said ionisable groups, moieties or monomers; kit and device comprising the material and process for preparation thereof; and use in detecting or sensing microbes or pH.

11 Claims, 5 Drawing Sheets

(51) Int. Cl.
| | | |
|---|---|---|
| A61F 15/00 | (2006.01) | |
| A61L 15/24 | (2006.01) | |
| A61L 15/26 | (2006.01) | |
| A61L 15/42 | (2006.01) | |
| G01N 31/22 | (2006.01) | |
| A61F 13/84 | (2006.01) | |
| A61B 5/145 | (2006.01) | |

(52) U.S. Cl.
CPC .......... *A61F 13/84* (2013.01); *A61F 13/8405* (2013.01); *A61F 15/001* (2013.01); *A61L 15/24* (2013.01); *A61L 15/26* (2013.01); *A61L 15/42* (2013.01); *A61L 15/425* (2013.01); *G01N 31/221* (2013.01); *A61B 2562/0295* (2013.01); *A61F 2013/00089* (2013.01); *A61F 2013/8473* (2013.01)

(58) Field of Classification Search
CPC .. A61F 13/00055; A61F 13/84; A61F 15/001; A61F 2013/00089; A61F 2013/8473; A61F 13/00021; A61F 13/0266; A61F 2013/00523; A61F 2013/427; A61B 2017/00035; A61B 5/14539; A61B 5/445; A61B 2562/0295; A61B 17/085; A61L 15/24; A61L 15/26; A61L 15/42; A61L 15/425; A61L 26/00; G01N 31/221
See application file for complete search history.

(56) References Cited

U.S. PATENT DOCUMENTS

| | | | |
|---|---|---|---|
| 3,675,654 | A | 7/1972 | Baker et al. |
| 3,759,261 | A | 9/1973 | Wang |
| 4,029,598 | A | 6/1977 | Neisius et al. |
| 4,192,311 | A | 3/1980 | Felfoldi |
| 4,382,380 | A | 5/1983 | Martin |
| 4,705,513 | A | 11/1987 | Sheldon et al. |
| 4,728,499 | A | 3/1988 | Fehder |
| 4,813,942 | A | 3/1989 | Alvarez |
| 4,885,077 | A | 12/1989 | Karakelle et al. |
| 4,999,306 | A | 3/1991 | Yafuso et al. |
| 5,104,660 | A | 4/1992 | Chvapil et al. |
| 5,181,905 | A | 1/1993 | Flam |
| 5,277,872 | A | 1/1994 | Bankert et al. |
| 5,536,783 | A | 7/1996 | Olstein et al. |
| 5,571,684 | A | 11/1996 | Lawrence et al. |
| 5,690,624 | A | 11/1997 | Sasaki et al. |
| 5,766,212 | A | 6/1998 | Jitoe et al. |
| 5,788,687 | A | 8/1998 | Batich et al. |
| 5,852,126 | A | 12/1998 | Barnard et al. |
| 5,853,669 | A | 12/1998 | Wolfbeis |
| 5,897,516 | A | 4/1999 | Kadash et al. |
| 6,120,904 | A | 9/2000 | Hostettler et al. |
| 6,284,942 | B1 | 9/2001 | Rabin |
| 6,333,093 | B1 | 12/2001 | Burrell et al. |
| 6,388,043 | B1 | 5/2002 | Langer et al. |
| 6,482,491 | B1 | 11/2002 | Samuelsen et al. |
| 6,617,488 | B1 | 9/2003 | Springer et al. |
| 6,688,525 | B1 | 2/2004 | Nelson et al. |
| 6,696,240 | B1 | 2/2004 | Kloepfer et al. |
| 6,747,185 | B2 | 6/2004 | Inoue et al. |
| 6,772,708 | B2 | 8/2004 | Klofta et al. |
| 6,815,207 | B2 | 11/2004 | Yabuki et al. |
| 7,159,532 | B2 | 1/2007 | Klofta et al. |
| 7,605,298 | B2 | 10/2009 | Bechert et al. |
| 7,622,629 | B2 | 11/2009 | Aail |
| 7,749,531 | B2 | 7/2010 | Booher |
| 7,777,092 | B2 | 8/2010 | Lykke et al. |
| 7,873,141 | B2 | 1/2011 | Imai et al. |
| 8,372,049 | B2 | 2/2013 | Jaeb et al. |
| 8,425,996 | B2 | 4/2013 | Gorski et al. |
| 8,791,315 | B2 | 7/2014 | Lattimore et al. |
| 8,795,257 | B2 | 8/2014 | Coulthard et al. |
| 8,808,274 | B2 | 8/2014 | Hartwell |
| 8,896,706 | B2 | 11/2014 | van den Hengel et al. |
| 8,927,801 | B2 | 1/2015 | Klofta |
| 8,997,682 | B1 | 4/2015 | Ashcroft |
| 9,311,520 | B2 | 4/2016 | Burg et al. |
| 9,445,749 | B2 | 9/2016 | Erickson et al. |
| 9,504,421 | B2 | 11/2016 | Greener |
| 9,829,471 | B2 | 11/2017 | Hammond et al. |
| 10,053,532 | B2 | 8/2018 | Hanson et al. |
| 10,058,455 | B2* | 8/2018 | VanDelden ....... A61F 13/00021 |
| 10,288,590 | B2 | 5/2019 | Hammond et al. |
| 11,027,043 | B1 | 6/2021 | Stockman et al. |
| 2002/0062114 | A1 | 5/2002 | Murai et al. |
| 2002/0091347 | A1 | 7/2002 | Eakin |
| 2004/0044299 | A1 | 3/2004 | Utsugi |
| 2004/0133090 | A1 | 7/2004 | Dostoinov et al. |
| 2005/0105789 | A1 | 5/2005 | Isaacs et al. |
| 2005/0187146 | A1 | 8/2005 | Helmus et al. |
| 2005/0199055 | A1 | 9/2005 | Browne |
| 2006/0140999 | A1 | 6/2006 | Lendlein et al. |
| 2007/0003606 | A1* | 1/2007 | Booher ............ A61F 13/00063 424/448 |
| 2007/0048224 | A1 | 3/2007 | Howell et al. |
| 2007/0129784 | A1 | 6/2007 | Lendlein et al. |
| 2007/0142762 | A1 | 6/2007 | Kaplan et al. |
| 2007/0188759 | A1 | 8/2007 | Mehendale et al. |
| 2007/0203442 | A1* | 8/2007 | Bechert ............ A61F 13/00063 602/52 |
| 2007/0225663 | A1 | 9/2007 | Watt et al. |
| 2007/0270774 | A1 | 11/2007 | Bergman et al. |
| 2007/0276207 | A1 | 11/2007 | Eagland et al. |
| 2008/0021166 | A1 | 1/2008 | Tong et al. |
| 2008/0208151 | A1 | 8/2008 | Zacharias et al. |
| 2009/0062757 | A1 | 3/2009 | Long et al. |
| 2009/0157024 | A1 | 6/2009 | Song |
| 2009/0190135 | A1 | 7/2009 | Clarizia et al. |
| 2009/0198167 | A1 | 8/2009 | Ambrosio |
| 2009/0216168 | A1 | 8/2009 | Eckstein et al. |
| 2009/0221977 | A1 | 9/2009 | Blott et al. |
| 2010/0041968 | A1 | 2/2010 | Meschisen et al. |
| 2010/0069838 | A1 | 3/2010 | Weber et al. |
| 2010/0112680 | A1 | 5/2010 | Brockwell et al. |
| 2010/0168695 | A1 | 7/2010 | Robles et al. |
| 2010/0168700 | A1 | 7/2010 | Schmidt et al. |
| 2010/0178203 | A1 | 7/2010 | Kane et al. |
| 2011/0274593 | A1 | 11/2011 | Gorski et al. |
| 2012/0123220 | A1 | 5/2012 | Iyer et al. |
| 2012/0201437 | A1 | 8/2012 | Ohnemus |
| 2012/0215190 | A1 | 8/2012 | Kawashima |
| 2012/0256750 | A1 | 10/2012 | Novak |
| 2012/0264163 | A1 | 10/2012 | Booher |
| 2012/0279101 | A1 | 11/2012 | Pretsch et al. |
| 2012/0323274 | A1 | 12/2012 | Lendlein et al. |
| 2013/0064772 | A1* | 3/2013 | Swiss ................ A61L 15/44 424/9.1 |
| 2013/0066285 | A1 | 3/2013 | Locke et al. |
| 2013/0066289 | A1 | 3/2013 | Song et al. |
| 2013/0087298 | A1 | 4/2013 | Phillips et al. |
| 2013/0131621 | A1 | 5/2013 | Van Holten et al. |
| 2013/0261409 | A1 | 10/2013 | Pathak et al. |
| 2013/0303865 | A1 | 11/2013 | Rebec et al. |
| 2013/0304006 | A1* | 11/2013 | Toth .................. A61B 5/14557 604/319 |
| 2014/0098209 | A1 | 4/2014 | Neff |
| 2014/0121487 | A1 | 5/2014 | Faybishenko et al. |

(56) References Cited

U.S. PATENT DOCUMENTS

| | | | |
|---|---|---|---|
| 2014/0138441 | A1 | 5/2014 | Davalos et al. |
| 2014/0154789 | A1 | 6/2014 | Polwart et al. |
| 2014/0296808 | A1 | 10/2014 | Curran et al. |
| 2015/0055134 | A1 | 2/2015 | Papautsky et al. |
| 2015/0080685 | A1 | 3/2015 | Markle et al. |
| 2015/0182166 | A1 | 7/2015 | Evans et al. |
| 2015/0265743 | A1 | 9/2015 | Hanson et al. |
| 2015/0308994 | A1* | 10/2015 | Hammond ........... G01N 31/221 436/163 |
| 2015/0351970 | A1 | 12/2015 | Dagger et al. |
| 2016/0100987 | A1 | 4/2016 | Hartwell et al. |
| 2016/0262672 | A1 | 9/2016 | Hammond et al. |
| 2017/0000407 | A1* | 1/2017 | Saxby ................ A61B 5/1032 |
| 2017/0183705 | A1 | 6/2017 | Hicks et al. |
| 2017/0234802 | A1 | 8/2017 | Hicks et al. |
| 2019/0015028 | A1 | 1/2019 | Hicks et al. |
| 2019/0212311 | A1 | 7/2019 | Hammond et al. |
| 2019/0358089 | A1 | 11/2019 | Dagger et al. |

FOREIGN PATENT DOCUMENTS

| | | |
|---|---|---|
| CN | 101453969 | 6/2009 |
| CN | 101490556 | 7/2009 |
| CN | 201414880 | 3/2010 |
| CN | 101894212 | 11/2010 |
| CN | 102879393 | 1/2013 |
| CN | 103217503 | 7/2013 |
| EP | 0 340 018 | 11/1989 |
| EP | 0 430 608 | 6/1991 |
| GB | 905040 | 9/1962 |
| GB | 1255395 | 12/1971 |
| JP | S54-176283 | 12/1979 |
| JP | S57-162304 | 10/1982 |
| JP | H07-055788 | 3/1995 |
| JP | 2002-165757 | 6/2002 |
| JP | 2003-210522 | 7/2003 |
| JP | 2004-239682 | 8/2004 |
| JP | 2005-123101 | 5/2005 |
| JP | 2006-338521 | 12/2006 |
| JP | 2007-163350 | 6/2007 |
| JP | 2012-157438 | 8/2012 |
| KR | 10 2006 0133139 | 12/2006 |
| KR | 20120059006 | 6/2012 |
| RU | 114854 | 4/2012 |
| WO | WO 1983/00742 | 3/1983 |
| WO | WO 1998/12996 | 4/1998 |
| WO | WO 1999/12581 | 3/1999 |
| WO | WO 2002/047737 | 6/2002 |
| WO | WO 2005/052572 | 6/2005 |
| WO | WO 2006/042871 | 4/2006 |
| WO | WO 2006/110502 | 10/2006 |
| WO | WO 2006/133430 | 12/2006 |
| WO | WO 2008/125995 | 10/2008 |
| WO | WO 2011/098575 | 8/2011 |
| WO | WO 2012/074509 | 6/2012 |
| WO | WO 2012/131386 | 10/2012 |
| WO | WO 2012/171922 | 12/2012 |
| WO | WO 2013/074509 | 5/2013 |
| WO | WO 2014/066913 | 5/2014 |
| WO | WO 2014/113770 | 7/2014 |
| WO | WO 2015/052219 | 4/2015 |
| WO | WO 2016/005288 | 1/2016 |
| WO | WO 2016/012219 | 1/2016 |
| WO | WO 2017/121871 | 7/2017 |
| WO | WO 2017/121873 | 7/2017 |

OTHER PUBLICATIONS

McLister et al., Molecular Wiring in Smart Dressings: Opening a New Route to Monitoring Wound pH. Healthcare, 2015, vol. 3, pp. 466-477 (Year: 2015).*

Van der Schueren et al., pH-sensitive textile sensors with possible use as wound dressings, Euromat, Abstracts, 2011 (Year: 2011).*

Chen, C. et al., "A PNIPAM-based fluorescent nanothermometer with ratiometric readout", Chemical Communications, vol. 47, No. 3, Nov. 26, 2010, in 3 pages.

Dargaville, T. et al., "Sensors and imaging for wound healing: A review," Biosensors and Bioelectronics, vol. 41, Mar. 2013, pp. 30-42, in 13 pages.

Great Britain Office Action and Search Report, re GB Application No. 1600746.2, dated Jul. 29, 2016.

Great Britain Office Action and Search Report, re GB Application No. 1600747.8, dated Dec. 1, 2016.

International Search Report and Written Opinion, re PCT Application No. PCT/EP2017/050711, dated Mar. 21, 2017.

International Preliminary Reporton Patentability, re PCT Application No. PCT/EP2017/050711, dated Jul. 26, 2018.

International Search Report and Written Opinion, re PCT Application No. PCT/EP2017/050704, dated Apr. 18, 2017.

International Preliminary Report on Patentability, re PCT Application No. PCT/EP2017/050704, dated Jul. 26, 2018.

Loh, B.Y. et al., "Automated Mobile pH Reader on a Camera Phone", IAENG International Journal of Computer Science, vol. 38(3), Aug. 2011, in 7 pages.

Reddy, T. et al., "Synthesis and Characterization of Semi-Interpenetrating Polymer Networks Based on Polyurethane and N-isopropylacrylamide for Wound Dressing", Journal of Biomedical Materials Research Part B: Applied Biomaterials, vol. 88B, No. 1, Sep. 8, 2008, in 9 pages.

Trupp, S., "Development of pH-sensitive indicator dyes for the preparation of micro-patterned optical sensor layers", Sensors and Actuators B, vol. 150, Jul. 15, 2010, pp. 206-210, in 5 pages.

Uchiyama, S. et al., "Fluorescent molecular thermometers based on polymers showing temperature-induced phase transitions and labeled with polarity-responsive benzofurazans", Analytical Chemistry, Amercial Chemical Society, vol. 75, No. 21, Oct. 4, 2003, in 10 pages.

"DuoDERM Signal Dressing—Time to Change", ConvaTec Ltd., dated Apr. 2009, in 2 pages. URL: https://marketingworld.convatec.com/MarketPortCore/MediaFile/DownloadByApplication?applicationToken=dc038e44b0b0ee4d8616f7b6880b24551bfecf237645a04fb5b76ab792a36858&itemId=aea404fa-f437-423a-a70b-bc96c5971e2d&mediaFileId=8531d794-0edf-45d4-b495-79ac8b21efca&forceDownload=true.

Cho, S.M. et al., "Thermo-sensitive hydrogels based on interpenetrating polymer networks made of poly(N-isopropylacrylamide) and polyurethane", Journal of Biomaterials Science, vol. 21 (8-9), 2010, pp. 1051-1068, in 18 pages.

Meier, R. J., "Luminiscent Single and Dual Sensors for In Vivo Imaging of pH and pO2", Doctoral Thesis submitted to University of Regensburg, Jun. 2011, in 187 pages.

Meier, R. J. et al., "Simultaneous Photographing of Oxygen and pH in Vivo Using Sensor Films", Angewandte Chemie International Edition, vol. 50(46), Nov. 2011, pp. 10893-10896, in 17 pages. URL: https://epub.uni-regensburg.de/21075/3/dissertation_Robert_J_Meier.pdf.

Mohr, G. et al., "Design of acidochromic dyes for facile preparation of pH sensor layers", Anal Bioanal Chem, vol. 392, pp. 1411-1418, in 8 pages.

* cited by examiner

Figure 2.1 Nile red under visible and ultraviolet (366 nm) light in different solvents
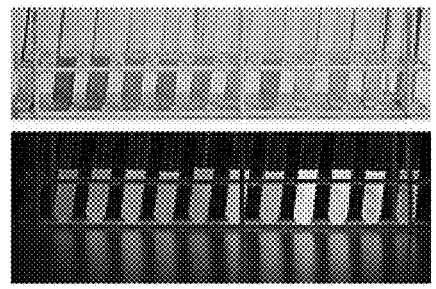
Figure 2.2 Fluorescent activity of dressing comprising polymer in PU foam supported on adhesive film
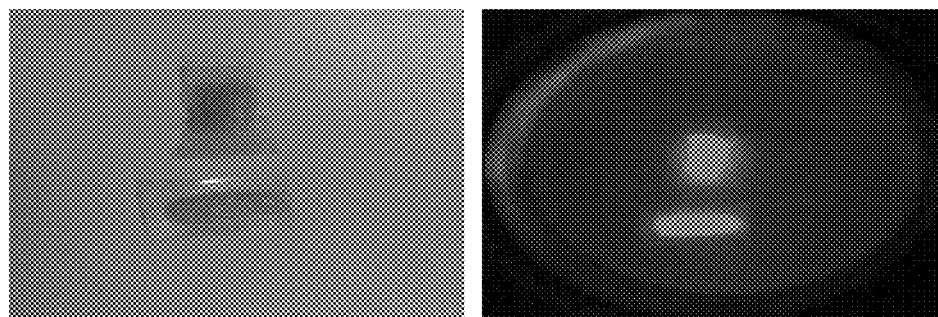
Figure 2.3 (a)
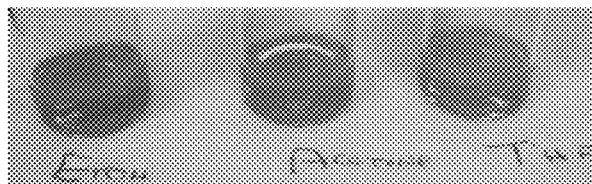
Sample 3.1.1 in ethanol, acetone and THF
Figure 2.3 (b)
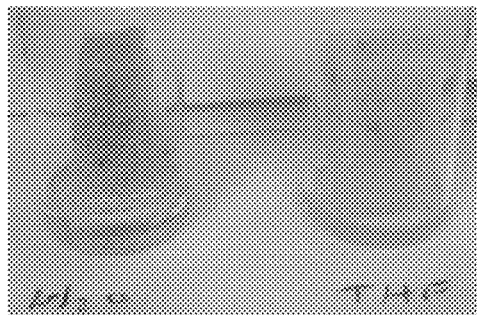
Sample 3.1.1 in deionised water and THF

Figure 3.1
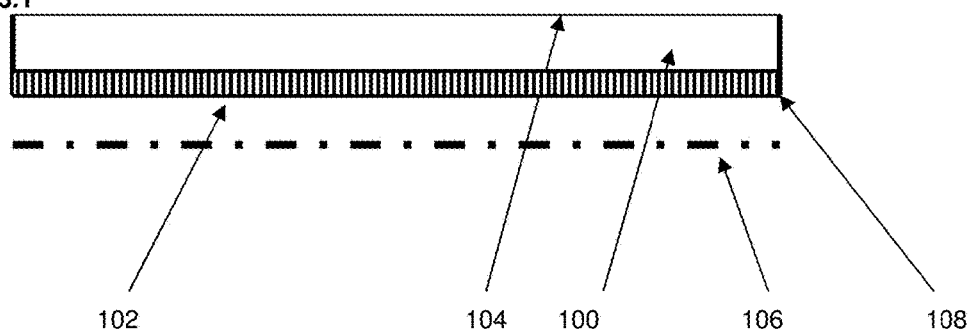
102   104 100   106   108
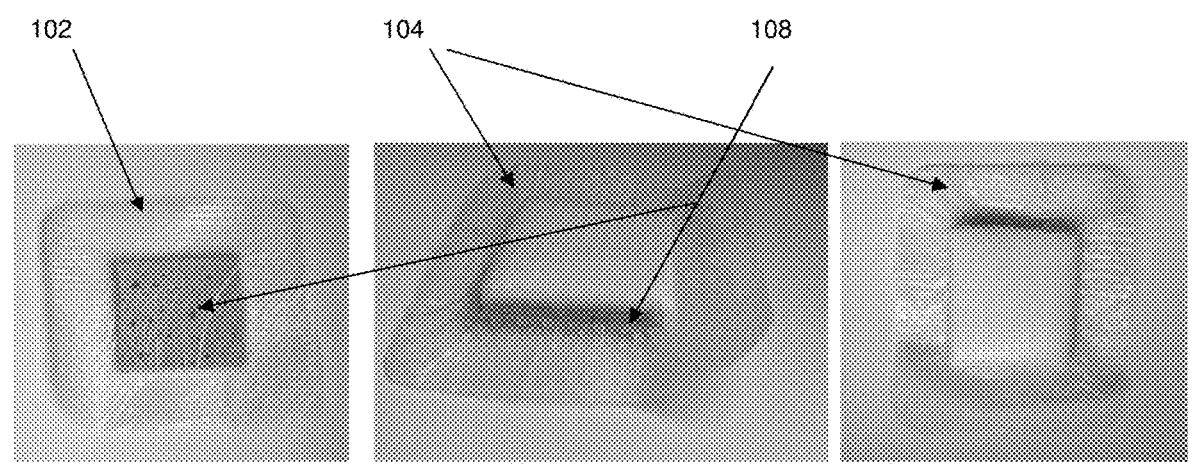
102   104   108
Figures 3.2.1 – 3.2.3

Figure 4 Flow scheme "use of device as indicator on wounds"
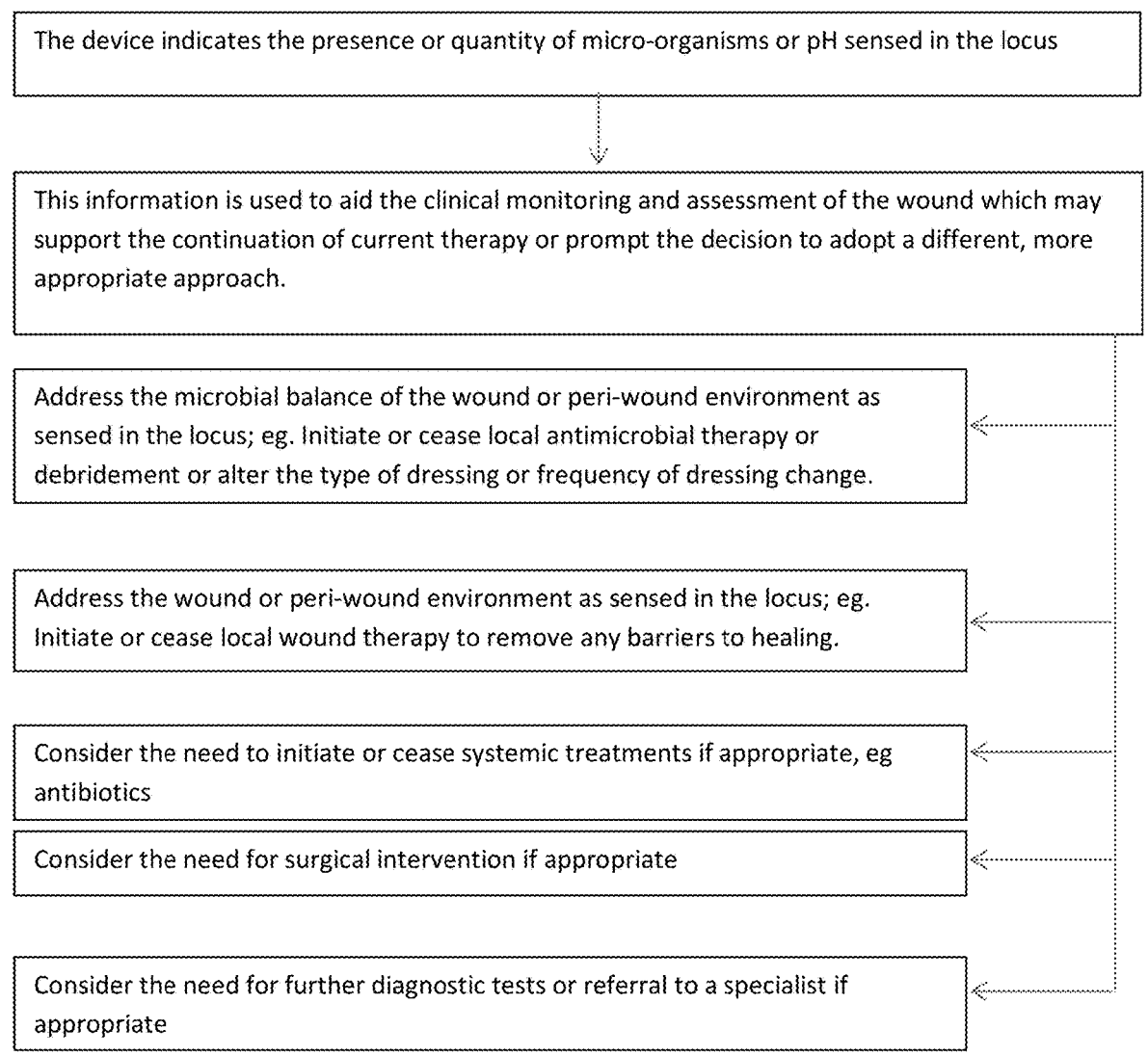

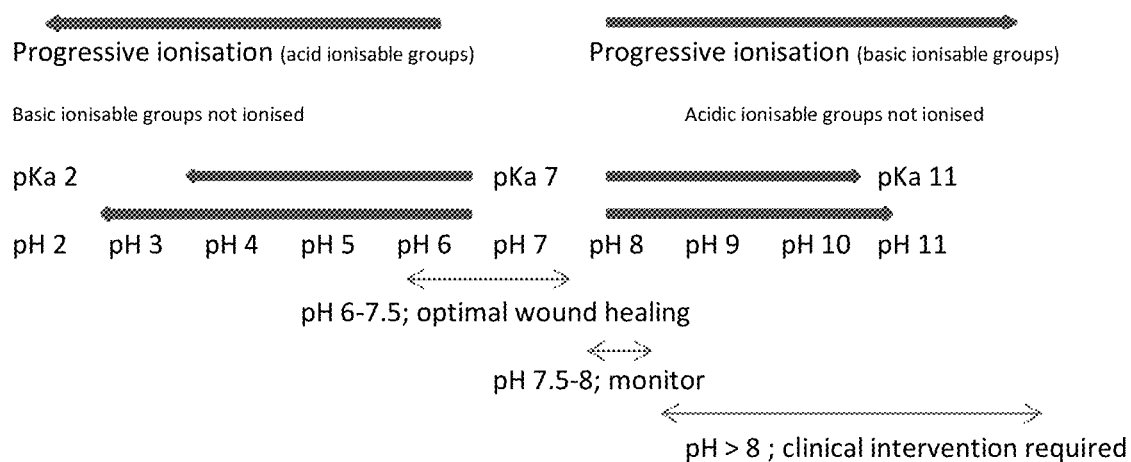
Figure 5 Calibration of device (Nile Red)

DEVICE AND KIT FOR INDICATING A PH AT A LOCUS

CROSS-REFERENCES TO RELATED APPLICATIONS

This application is a national stage application of International Patent Application No. PCT/EP2017/050704, filed on Jan. 13, 2017, titled "DEVICE AND KIT FOR INDICATING A PH AT A LOCUS," which claims priority to GB Patent Application No. GB1600747.8, filed Jan. 14, 2016, titled "IMPROVEMENTS IN AND RELATING TO DEVICES"

FIELD OF INVENTION

The present invention relates to pH indicating material and a device comprising the same, preferably for sensing or detecting microbes at a locus, comprising polyurethane polymer material comprising a polyurethane network polymer wherein the network comprises immobilised pH responsive hydrophilic copolymer; a construct or wound dressing comprising the material; novel hydrophilic copolymers, processes for their preparation, a kit comprising a device, construct or wound dressing and a device for inspection thereof, methods for detecting and/or sensing microbes and their use for example in medical care, dental care, sanitation, point of use sterilisation, hygiene, personal care, biosurveillance or packaging.

BACKGROUND

The field of wound care management has long understood that the pH of a wound can be an indication of wound healing status and can indicate when further action may be necessary to aid wound healing. It is therefore important to be able to monitor wound pH in order to be able to assess wound healing and intervene, if necessary.

At present any dressing would need to be removed and the wound inspected to determine if the wound is infected thus exposing the wound to further bacteria and potential complications. Invasive sampling such as by tissue biopsy, withdrawing a swab or wound fluid sample for testing, investigating pH by probe and the like is the usual means to confirm presence of infection. Whilst a pH probe allows direct measurement of the pH at the wound surface, its use can result in tissue disruption and localised cell death, and the probe requires regular calibration. Moreover, the measurement only provides a snap-shot of the pH of a specific area of the wound at a single point in time and provides no indication of the pH changes over time.

Some currently available wound dressings utilize a pH indicator dye provided on a colour strip integrated within the dressing. The dye changes colour (e.g., from yellow to purple) if the pH value is between 6.5 and 8.5, an indication of an infected wound. The dye is not sufficiently sensitive to provide an indication of the incremental change in pH between 6.5 and 8.5. Additionally, the dye does not provide an indication of the pH at the wound surface but rather the pH of the wound exudate precisely at the colour strip where it is detected. As the pH of wound exudate can vary extremely locally across a wound the measurement of the pH of wound exudate at only one point risks missing important information about wound health or even giving a false impression of wound health. pH of wound exudate can also be affected by numerous external factors, including the composition of the dressing itself, and therefore to rely on wound exudate being transported within the dressing to the colour strip may introduce inaccuracies.

Adding pH indicating functionality to otherwise non-active polymeric devices and surfaces is an attractive proposition for detecting infection across a wound. Adding functionality to polyurethanes, which are used extensively as wound dressing materials, would be particularly beneficial. Polyurethanes present the opportunity to introduced functional additives in the course of their preparation by polymerisation of isocyanates and alcohols and/or water. Adding functional additive to polyurethane in this manner is known for the purpose of delayed or controlled additive release into a locus.

BRIEF DESCRIPTION OF THE INVENTION

We have now surprisingly found that pH indicating function may be immobilised in polyurethane and retained therein throughout the duration of contact with a locus at which pH is to be indicated. In particular we have found that hydrophilic copolymer, incorporating useful pH indicating function, may be immobilised in polyurethanes by mixing in during polyurethane polymerisation, more particularly during or prior to network formation such as during or prior to a chain extending step or a crosslinking step or during a step growth polymerisation step. A polyurethane network is generated in the presence of the hydrophilic copolymer. The hydrophilic copolymer is immobilised in the network, attributed in some part to it becoming entwined within, and penetrated by, the network whereby it is unable to diffuse out of the polyurethane network.

The present invention relates to the improvement of polymer materials and devices, more particularly wound dressings, with the use of polymer material comprising a polyurethane polymer network comprising immobilised within the network a hydrophilic copolymer comprising one or more pH sensitive functional groups or moieties. The hydrophilic copolymer is not leached or extracted from the polyurethane polymer network. Preferably the polymer material is a polyurethane polymer material of a polyurethane polymer network comprising immobilised therein a hydrophilic copolymer of a hydrophilic monomer and one or more pH sensitive monomers. Hereinbelow, hydrophilic monomer may be the same as or different to pH sensitive monomer.

The device provides indication of pH directly in real time for example at point of care, and provides indication of pH changes over time. The device allows non invasive pH indication, i.e. without the need to investigate by probe or sample. The device provides pH at increments for example dependent on calibration. The device moreover provides indication of pH over an area, such as a surface, for example providing a pH map or microbe map at a locus.

In an embodiment there is provided herein a device for indicating pH at a locus in the range pH 5 to pH 10, preferably as indication of presence of microbes, comprising a surface configured to contact the locus, wherein the device comprises polyurethane material distributed in relation to said surface, which material comprises
a polyurethane network having immobilised therein one or more hydrophilic copolymers, the or each said copolymer comprising:
hydrophilic monomer; and
one or a plurality of ionisable groups or moieties having one or more characteristic pKa values in the range 2 to 12;
wherein hydrophilic state of hydrophilic copolymer is affected by ionisation of said ionisable groups or moieties;

and wherein the or each said copolymer further comprises indicator monomer which provides indication of hydrophilic state of said hydrophilic copolymer.

The one or more ionisable groups or moieties may be provided by one or more ionisable monomers. Ionisable functional group or moiety is suitably ionisable monomer. The material may comprise a plurality of ionisable groups or moieties provided on one copolymer or provided on each of a plurality of copolymers. An ionisable monomer may comprise one or a plurality of ionisable groups or moieties.

In a particular advantage the polyurethane material is obtained in a simple manner that involves only blending of hydrophilic copolymer with polyurethane prepolymer, prior to or during the polyurethane network generating reaction. Hydrophilic copolymer is immobilised in the polyurethane network by mixing in during the polymerisation reaction. More particularly the hydrophilic copolymer appears to become entwined within, and penetrate, or become entangled by, the network whereby it is unable to diffuse out of the polyurethane network.

Ionisable functional group or moiety or monomer are suitably selected from acid and/or base functional groups and moieties and monomers which are sensitive to pH of locus.

In an embodiment the material as hereinbefore defined comprises ionisable acid groups or moieties and ionisable base groups or moieties as defined.

Ionisable functional group or moiety as defined is suitably ionisable monomer. Ionisable monomer is suitably selected from one or more acid monomers, one or more base monomers and a combination of one or more acid monomers and one or more base monomers.

In an embodiment the material as hereinbefore defined comprises one or more ionisable base monomers.

The device is preferably for sensing or detecting microbes by means of intimate contact with a locus. Microbes are preferably selected from bacteria, yeast, fungi, and combinations thereof.

The device preferably includes a surface configured to contact the locus, such as a wound and is adapted to be in fluid communication with the locus, such as a wound. The polyurethane material provides a hydrophilic environment facilitating intimate fluid communication.

The device suitably provides a first indication, such as colour or intensity or lack thereof, prior to contact with the locus or fluid communicating with the locus, such as a wound or wound exudate and changes indication along a spectrum as a function of pH, for example the pH of locus or fluid such as wound or wound exudate. Preferably response to pH and indication thereof is reversible and indicates pH as a function of time.

Wound treatment often involves monitoring a wound during healing for indications of the status and progress of the wound. Monitoring indications of wound health can indicate the efficacy of delivered treatment or signal to a physician a need for a change in treatment. One indicator in particular that is useful for this monitoring is the pH level of the wound tissue.

The pH of tissue can indicate or affect a number of factors relevant to wound healing including oxygen release, angiogenesis, protease activity and bacterial toxicity. Acute and chronic wounds with an elevated alkaline pH have been shown to have lower rates of healing than wounds in which the pH is closer to neutral. For example, if a chronic wound has a pH of between 6 to 7.5 this indicates that wound healing is progressing well. In comparison, if the pH is between 7.5 and 8, this indicates that the wound should be monitored and a pH of above 8 indicates that clinical intervention is required.

The term "pKa" used herein is defined as the negative logarithm of the acid dissociation constant (Ka) of an acid. The acid dissociation constant, Ka, is defined as $[H^+][A^-]/[HA]$, wherein [HA] denotes the concentration of undissociated acid, HA, in a solution and, $[H^+]$ and $[A^-]$ denote the concentrations of hydrogen ion, $H^+$, and anion, $A^-$, thereof in the solution. Consequently the value of pKa can be obtained from the equation: $pKa=-\log [H^+]-\log([A^-]/[HA])= pH-\log([A^-]/[HA])$. In the present context, pKa may be used to describe the hydrophilic copolymer or polyurethane material or device itself or the ionisable group or moiety or polymerisable ionisable monomer used to prepare the hydrophilic copolymer, material or device.

In embodiments the ionisable monomer is responsive to pH between pH5 and 10 and the indicating monomer indicates changes in hydrophilic state of hydrophilic copolymer, affected by changes in ionisation in turn responsive to changes in pH, by way of a colour change and/or intensity change along a colour and/or intensity spectrum, with each colour and/or intensity in the spectrum being associated with a particular pH. In embodiments, the device or material is able to detect wound pH between about pH 5 and about pH10. Particularly, ionisable groups or moieties or monomer has characteristic pKa in the range 2 to 5.5 and/or 5.5 to about 9.5 and the device or material is able to detect wound pH between about pH 5.5 and about pH 9.5. More particularly, ionisable groups or moieties or monomer has characteristic pKa in the range between about 2 and 5 and/or 6.5 and about 9.5 and the device or material is able to detect wound pH between about pH 6.5 and about pH 9.5.

In embodiments, the polyurethane material comprises a combination of ionisable groups, moieties or monomers. This allows a broader pH range to be detected than can be detected by use of a single group, moiety or monomer. In embodiments the device or material comprises a blend of hydrophilic copolymers of a number of ionisable monomers having different characteristic pKa. In further embodiments the device or material comprises hydrophilic copolymer comprising a number of ionisable monomers having different characteristic pKa.

In embodiments, the device or material changes colour or intensity in response to change in pH and this change is detectable at, for example, intervals of about a 0.1 unit, about 0.2 unit, about 0.3 unit about 0.4 unit or about 0.5 unit interval of pH. It is envisaged that the detection level will vary based on the type of detection means utilised. For example, an electronic detector such as a colour or intensity meter, has the capability to detect a 0.1 unit change in pH. In comparison, the human eye is only capable of visually detecting a colour or intensity change which is associated with about a 0.5 unit change in pH. In a wound care setting, wound exudate pH can be detected across a broad range.

In embodiments, the pH indicator utilised in the device is able to detect the pH between about pH 5 and about pH 10 and indicates changes in pH by way of a colour or intensity change along a spectrum, with each colour or intensity in the spectrum being associated with a particular pH. In embodiments, the pH indicator is able to detect wound pH between about pH 5.5 and about pH 9.5. More particularly the pH indicator is able to detect wound pH between about pH 6.5 and about pH 9.5.

Functional groups bear charge or are uncharged at different pH; acid groups are charged at high pH or uncharged at low pH and base groups uncharged at high pH and charged at low pH; change in pH from high to low pH or low to high pH causes change in hydrophilicity of polymer, indicated by indicator as a change in intensity or colour.

In embodiments, the pH indicator utilised in the device is able to detect the pH between about pH 5 and about pH 10 and indicates concentration or change in concentration of acid or base species by way of a colour or intensity change along a spectrum, with each colour or intensity in the spectrum being associated with a particular concentration. In embodiments, the pH indicator is able to quantify wound health or wound status, such as extent of wound ill health.

In a further aspect there is provided a pH responsive calibrated device comprising material as hereinbefore defined. A calibrated device characterised by pKa of ionisable group, moiety or monomer is calibrated according to hydrophilic state at different pH and indication of indicator monomer at different hydrophilic states.

Change in pKa of ionisable group or moiety or monomer may result on incorporation in hydrophilic copolymer or on incorporation of hydrophilic ionisable copolymer in polyurethane network. Change may be dependent on location in network, steric factors, neighbouring groups and the like. Material may comprise a plurality of ionisable groups, moieties or monomers having different characteristic pKa. Changes induced by ionisation event may vary quite significantly according to hydrophilic ionising copolymer. Change in polymer characteristics is in some cases abrupt and in some cases gradual. A calibrated device as hereinbefore defined is mapped according to changes induced in hydrophilicity at specific pH points. A detailed understanding of the polymer characteristics may therefore not be required.

In an embodiment there is provided a pH responsive calibrated device for indicating pH at a locus in the range pH 5 to pH 10, preferably as indication of presence of microbes, comprising a surface configured to contact the locus, wherein the device comprises polyurethane material distributed in relation to said surface, which material comprises a polyurethane network having immobilised therein one or more hydrophilic copolymers, the or each said copolymer comprising:
hydrophilic monomer; and
one or a plurality of ionisable groups or moieties having one or more characteristic pKa values in the range 2 to 12;
and wherein the or each said copolymer further comprises indicator monomer which provides indication of hydrophilic state of said hydrophilic copolymer;
characterised by characteristic pKa or by aggregate pKa being the difference in pKa of respective acid and/or base groups and moieties, calibrated according to hydrophilic state at different pH and indication of indicator monomer at different hydrophilic states. Preferably the device is a device as hereinbefore defined.

This may be represented in the relation: pH=aggregate pKa=(pKa base−pKa acid)=Hydrophilic state=colour or intensity; and/or
[acid or base detected]=aggregate pKa=(pKa base−pKa acid)=Hydrophilic state=colour or intensity.

In each relation=represents a correspondence or proportionality, the sequence of stages in each relation, as a whole, representing a calibratable relation between pH or concentration of acid or base detected and colour or intensity.

Aggregate pKa may be a non-linear sum or difference of component pKas. pKa of a group or moiety may be affected by factors including concentration and quantity of acid and/or base groups or moieties having a given pKa, and steric factors of such groups or moieties and the like. Progressive ionisation of groups or moieties having a given pKa, in response to change in pH or concentration of acid or base detected, may influence ionisation of further groups or moieties having same or different pKa.

Aggregate pKa may therefore differ at any given pH or concentration of acid or base at a given pH.

This may also be represented as in FIG. 5 in which a nominal relation has been assigned to the relation of pH and aggregate pKa, and to the relation of respective pKas for simplicity.
eg pH 8.5=aggregate pKa 8.5=pKa 4-pKa 11.5=Hydrophilic state=colour
eg pH 6=aggregate pKa 6=pKa2-pKa10=Hydrophilic state=colour.

The calibrated device is calibrated according to the observation that material is hydrophilic at low pH and high pH by virtue of charged acid and base ionisable groups such as —COOH and —NH3 groups, and is hydrophobic at neutral or intermediate pH by virtue of uncharged ionisable acid and base groups.

Hydrophobic state corresponding to pH >8 may be created by means of a blend of pH responsive groups of acid and base character, giving aggregate pKa.

A device as hereinbefore defined or a sensor comprising said device may be calibrated to omit any indication or signal in a given pH range, for example in range pH 6-7.5 whereby any colour signal corresponding to hydrophilic state in this range is indicative of the equivalent basic hydrophilicity. This is readily achieved by incorporation of peptides.

A device as hereinbefore defined or a sensor comprising said device may be calibrated as an acidic and basic pH sensor or one only thereof. Preferably the device is a universal pH sensing or indicating device. Alternatively the device or a sensor comprising said device is an acidic pH sensor or a basic pH sensor. Characteristic pKa may be such as to give an aggregate pKa in either an acid range or a basic range whereby a change in hydrophilic state is attributable to acid ionisation events or basic ionisation events. Alternatively changes in hydrophilic state in acid and in base range are distinguishable.

Preferably the device as hereinbefore defined or a sensor comprising said device indicates acidic pH <6, neutral and/or basic pH.

The material or device is ideally suited for use with an inspection or scanning device or reader as described in WO2016/01229, the contents of which are incorporated herein by reference, for inspecting or scanning or reading the detection device and displaying information relating to sensed or detected microbes such as bacteria or pH, for example for displaying an image or information relating thereto. The detection device is conveniently provided together with a separate or integral inspection or scanning strip providing reference information to facilitate generating output information relating to bacteria or pH. Our finding has moreover enabled the provision of a method for inspection or scanning as disclosed therein and as disclosed in WO 2015/110411, the contents of which are incorporated herein by reference.

With the current invention the wound dressing may not need to be removed to determine the type of bacteria (gram positive or gram negative) that is present and the amount present.

Presence of infection may be evidenced by visual inspection or scan in situ of the device or material such as a dressing cover layer or wound contact layer, for change in appearance thereof. This will be done either visually through a colour change of the dressing or by an optical reader. It may be necessary to remove opaque dressings and examine the wound facing side either visually or by use of an optical reader. Preferably the material and device enable identification and quantification of bacteria.

Microbial or microbes herein include bacteria or bacteria, yeast, fungal, fungus or fungi or combinations thereof.

In preferred embodiments there is provided a device comprising polyurethane material for indicating pH at a locus in the range 5 to 10 and for sensing or detecting microbes at the locus,
comprising a surface configured to contact the locus,
wherein the material comprises a polyurethane network having immobilised therein one or more hydrophilic copolymers, the or each said copolymer comprising:
hydrophilic monomer; and
indicator monomer, which provides an indication in response to a change in hydrophilic state of hydrophilic monomer and/or hydrophilic copolymer;
wherein the polyurethane network is generated in the presence of and about the hydrophilic copolymer(s);
characterised in that the or each copolymer further comprises one or a plurality of acid functional groups and/or base functional groups having one or more characteristic pKa values in the range 2 to 12
and in that response of said acid and/or base functional groups induces a change in hydrophilic state.

In a further aspect there is provided a device for sensing or detecting microbes at a locus, comprising a surface configured to contact the locus, wherein the device further comprises polyurethane material as hereinbefore defined.

Preferably the device comprises in addition to the locus-contacting surface, an opposing non-locus contacting surface, wherein either surface or both comprises one or more pH indicating zones comprising a polyurethane material as hereinbefore defined.

The surface may be a polyurethane material surface or the polyurethane material may be applied to a locus contacting surface. The surface may comprise polyurethane material at a face thereof configured to contact the locus or at an opposing face thereof.

The surface and/or the material is suitably fluid permeable at least on a locus contacting face thereof. The surface and/or the material may be fluid permeable throughout. The surface and/or material and/or device may be fluid impermeable at an opposing face thereof.

The device may be rigid or conformable. Preferably the device is conformable. The surface may be planar or shaped, preferably is planar for example is sheet-form. The device may be configured for immersing in a locus or applying to a surface of a locus. Preferably the device is for applying to a surface of a locus.

A locus as hereinbefore defined, which may comprise or be provided in an environment as hereinbelow referred, preferably comprises or contains or consists of fluid, in particular aqueous fluid including moisture and physiological fluids. The device is preferably configured to be in fluid communication with the locus. Preferably a locus is a moist locus such as an exuding locus. A device as hereinbefore defined may be activated by fluid contact.

The hydrophilic copolymer may be branched or linear or part(s) or moiety/moieties thereof may be branched and part(s) or moiety/moieties thereof may be linear. Branched includes moderately branched, highly branched or hyper branched and combinations thereof.

Suitably the material or device comprises non-leachable hydrophilic copolymer.

Preferably therefore such device is not intentionally anti biotic. Preferably the device or material are configured to interact with live microbes such as bacteria via fluid communication with fluid.

Preferably microbes such as bacteria are substantially unchanged by interaction with the device or material, at least in terms of antibiotic resistance. Without being limited to this theory it is thought that microbes such as bacteria are not disrupted by interaction with the device, at least to an extent that might induce antibiotic resistance, or are not violated or entered as a result of contact with the device, at least to an extent that might induce antibiotic resistance.

Preferably the device is not configured to release microbicide such as bactericide or antibiotic which might permanently interact with microbes or bacteria.

Preferably the device or material are not classified as antibiotic nor contemplated as having the capacity to contribute to the risk of developing antibiotic resistance.

Hydrophilic copolymer is immobilised within the polyurethane polymer network as hereinbefore defined. Reference herein to immobilisation or to hydrophilic copolymer being immobilised within or by the polyurethane polymer network is to its presence within the network and remaining within the network throughout the intended use or lifetime of the device or material or subject to the conditions of an intended locus for use thereof.

Preferably hydrophilic copolymer and thereby indicator is distributed throughout the surface of the device or material. Hydrophilic copolymer and thereby indicator are thus characterised by location at the surface of the device or material. Hydrophilic copolymer and/or indicator may be associated with or may provide location information. Location information may for example be in the form of a device map or surface map. For example indicator may provide location information for indication or change of indication such as a device map or surface map of indication or change of indication. Suitably indicator is adapted to detect or sense pH in the direct vicinity thereof.

Preferably hydrophilic copolymer remains immobilised in the presence of water, aqueous media or physiological fluid and the like at ambient temperature such as in the range 0-45 C, most particularly under physiological conditions.

Immobilised hydrophilic copolymer is thus retained within or on the device or material. Hydrophilic copolymer is thus able to sense, detect or indicate microbes present or pH at the surface. Immobilised hydrophilic copolymer, may be retained at one or a plurality of zones within or on the device or material. Hydrophilic copolymer is thus able to sense, detect or indicate bacteria or pH at the zone.

In a particular advantage the polyurethane material is obtained in a simple manner that involves only blending of hydrophilic copolymer with polyurethane prepolymers or precursors.

Preferably therefore the hydrophilic copolymer is immobilised within the network by introduction during the polymerisation reaction, which may be during formation of prepolymer or step growth of the polyurethane network whereby the hydrophilic copolymer is present during the growth of the network, or during chain extension or cross-linking thereof.

Indication as hereinbefore defined indicates microbes or pH by means of an optical change, a molecular or phase change, or a change in adsorption or emission spectra in the UV, visible or Infra red regions of the electromagnetic spectrum.

Conveniently change of indication is displayed as an optical change such as a change in colour, more particularly as a change in fluorescence, or intensity, quantity or magnitude or signal thereof, most preferably as a change in fluorescence wavelength or fluorescence intensity.

A device as hereinbefore defined is preferably configured for detecting or sensing bacteria present in or comprised at a locus or in an environment preferably in an environment comprising or containing or consisting of or associated with fluid, in particular aqueous fluid including aqueous liquids and vapours such as moisture and physiological fluids. The device is preferably configured to be in fluid communication with such environment. Preferably such environment is a moist environment such as an exuding or humid environment, for example an exuding or humid wound environment or an associated environment such as a wound fluid reservoir or conduit. A device as hereinbefore defined may be activated by fluid contact

DESCRIPTION OF THE FIGURES

FIG. 2.1 illustrates Nile red under visible and ultraviolet (366 nm) light in different solvents (From left to right: 1. water, 2. Methanol, 3. Ethanol, 4. Acetonitrile, 5. Dimethylformamide, 6. acetone, 7. Ethyl acetate, 8. Dichloromethane, 9. n-hexane, 10. Methyl-tert-butylether, 11. Cyclohexane, 12. Toluene);

FIG. 2.2 illustrates fluorescent activity of material in a device herein;

FIGS. 2.3(a) and 2.3(b) illustrate sample materials in ethanol and other solvents;

FIGS. 3.1 and 3.2 illustrate a device or dressing herein;

FIG. 4 illustrates a flow scheme using the device as indicator on wounds;

FIG. 5 illustrates calibration of material and device herein.

DETAILED DESCRIPTION

Polyurethane Material

Figure 1:
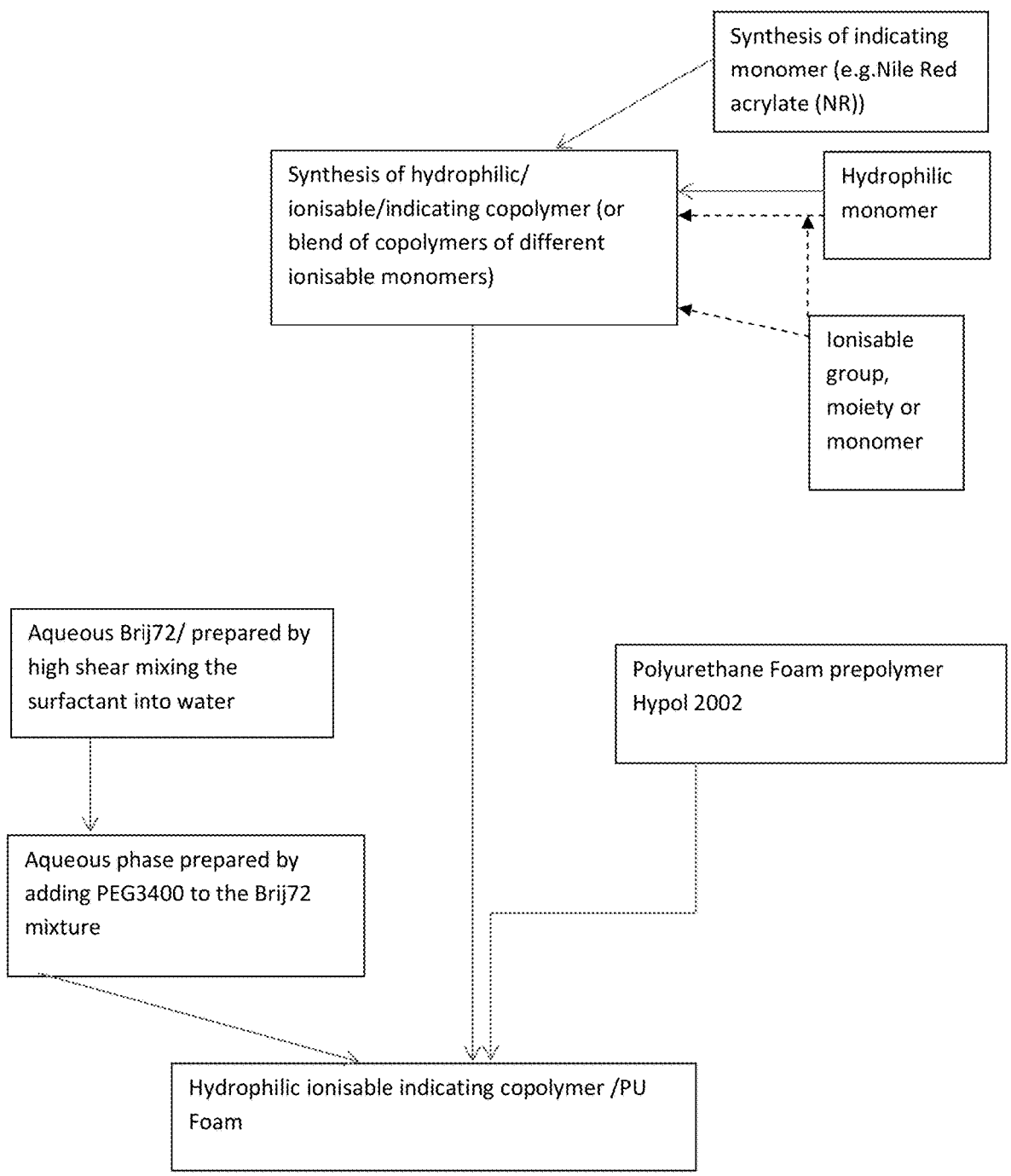
FIG. 1 illustrates a scheme for the preparation of herein defined polyurethane material.

Hydrophilic copolymer is immobilised by means of interpenetrating network (IPN), more particularly entrapped semi-IPN or other feature resulting from network formation in the presence of hydrophilic copolymer Polyurethane material may be in any form suited for the intended purpose. Preferably polyurethane material is in the form of a foam, film, perforated film, membrane, water impermeable membrane providing moisture vapour transmission (MVT), adhesive layer or coating, sheet, block, non-woven or woven fabric, fibers and the like and combinations thereof.

Polyurethane material in a form as hereinbefore defined may be foamed, unfoamed or xerogel.

A foam is preferably open cell as known in the art. We have found that a polyurethane foam formation is not disrupted by the presence of the hydrophilic copolymer.

A xerogel is a solid formed from a gel by drying with unhindered shrinkage. Xerogels usually retain high porosity (15-50%) and enormous surface area (150-900 m$^2$/g), along with very small pore size (1-10 nm).

Xerogels are well suited to the immobilisation of hydrophilic copolymer as hereinbefore defined in gel form. An adhesive layer or coating of material as hereinbefore defined may be applied to a device or part thereof as a gel, more preferably a xerogel, as known in the art.

Preferably polyurethane material possesses the facility to conform to or be deformed or conformed to fit or cover a locus such as a wound surface. Conformable material possesses the advantages of facilitating mapping of species across a surface for example mapping bacteria or pH profiles across a locus, in particular a wound. This has clear benefits over detecting bacteria or pH at isolated locations. Mapping is particularly advantageous as the pH or bacteria in a wound is often not uniform across the wound. Importantly it is surmised that all wounds contain sub critical levels of bacteria, however as the population increases it reaches a detrimental magnitude in the wound which is classified in order of severity as contaminated, colonised, critically colonised and ultimately as infection level. These levels are given the meaning known in the art. Advantages are also apparent in the use of the herein defined polyurethane materials in relation to systems from which bacteria can readily propagate and for which it is desired to rapidly identify the source or epicentre of detected bacteria or their population, such as in relation to wounds, air conditioning systems, water management systems and the like. Polyurethane material in the form of conformable cover material as hereinbefore defined confers the facility to detect the location of a bacterial population which is of detrimental magnitude.

Polyurethane Network Polymer

Preferably polyurethane network polymer is the product of reaction of an isocyanate terminated monomer and a long chain did and/or polyol. Reaction generates the isocyanate terminated oligomeric prepolymer. The polyurethane network is the result of chain extension or crosslinking said isocyanate terminated oligomeric prepolymer, with use of chain extending long chain did and/or polyol or crosslinking agent which may be introduced simultaneously with or subsequent to the polymerisation reaction.

Isocyanate terminated monomer may be aromatic or aliphatic. Preferably aromatic isocyanate terminated monomer is selected from one or more of toluene diisocyanate (TDI), methylenediphenyl isocyanate (MDI), para phenylene diisocyanate (PPDI) and naphthalene diisocyanate (NDI).

Preferably aliphatic isocyanate terminated monomer is selected from one or more of hexamethylene diisocyanate and dicyclohexyl methyl diisocyanate (hydrogenated MDI) and the like.

Long chain did or polyol is conveniently selected from one or more polyols or diols of polyester, polycaprolactone, polyether and polycarbonate, more preferably the polyols thereof. For example polyether long chain polyol is selected from polytetramethylene ether glycol (PTMEG), polyoxypropylene glycol (PPG) and polyoxyethylene glycol (PEG).

Isocyanate terminated monomer and long chain did or polyol are conveniently provided in the form of an isocyanate terminated polyether prepolymer thereof for example as commercially available in the range of HYPOL® polyurethane prepolymers (W R Grace & Co). HYPOL® prepolymer includes prepolymer of aromatic or aliphatic isocyanates and long chain did or polyol.

HYPOL® derived polyurethane foams may be prepared by reacting the isocyanate terminated polyether prepolymer with water or aqueous phase.

Non-foamed HYPOL® derived polyurethane products such as blocks, films, membranes or the like may be prepared by reacting the isocyanate terminated polyether prepolymer with diol or polyol.

Essentially non aqueous polyurethane such as xerogel may be prepared by reacting a prepolymer of a polyisocyanate and a polyol such as a glycol such as diethylene glycol or low molecular weight polyethylene glycol or polypropylene glycol (PEG or PPG). Such polyisocyanate may be an aliphatic polyisocyanate. Such polyisocyanate is commercially available for example as Desmodur N100.

Hydrophilic Copolymer

Change in hydrophilic state of hydrophilic monomer, hydrophilic copolymer or polyurethane material as appropriate is suitably reversible.

Suitably the hydrophilic copolymer is combined with the polyurethane components prior to casting into a mould or onto a surface. Polyurethane material may be cast into a mould or onto a surface to form a foamed or non foamed block or sheet, gel, membrane or film, or to form fibers or the like.

It is one benefit of the invention that hydrophilic copolymer may be simply blended with polyurethane network polymer prepolymers or precursors during the reaction thereof and prior to chain extension or crosslinking, whereby it is immobilised within the polyurethane network. Hydrophilic copolymer may be blended with one of the polyurethane components or ingredients prior to combining the respective components or ingredients. For example hydrophilic copolymer may be combined with an isocyanate component or polyol component or both such as the HYPOL phase or the long chain diol and/or polyol phase in a polyurethane system.

Preferably the hydrophilic copolymer is provided in fluid phase, preferably dissolved in solvent prior to combining with one or more polymerisation reaction prepolymers or precursors or dissolved or solvated in situ in one or more thereof. Hydrophilic copolymer introduced in dissolved form is more readily able to form an interpenetrating or entangled network with the polyurethane polymer.

Hydrophilic copolymer adopts a hydrophilic state. Indicator monomer is responsive to change of hydrophilic state of proximal copolymer, typically a decrease or increase in hydrophilicity, initiated by ionisation or reverse ionisation of pH responsive ionisable group, moiety or monomer at elevated pH such as in microbial environments. Change in hydrophilicity may be local, i.e. may occur within or specific to zones of the hydrophilic copolymer and thereby within or specific to zones of the polyurethane material.

Hydrophilic copolymer may be provided in the polyurethane material in any desired amount. Hydrophilic copolymer may be present in an amount from a trace amount up to the maximum amount which the crosslinking or chain extension process or any shaping process such as foaming tolerates. Preferably hydrophilic copolymer is present in an amount greater than or equal to a trace amount, preferably in an amount of from 0.01 wt % up to 20 wt %, such as from 0.1 wt % up to 20 wt %. preferably from 1 wt % up to 20 wt %, preferably 4-20 wt %, for example 4-15 wt %.

Hydrophilic copolymer is suitably present uniformly distributed throughout the polyurethane polymer network. Configuration of the polyurethane material within a device or wound dressing may be in layers, films, patches, windows or the like. This may for example facilitate greater distribution with relatively lower loading.

Attachment of Monomers and Architecture of Copolymer

Hydrophilic monomer, indicator monomer and ionisable monomer suitably comprise mutually reactive attachment sites or groups. Attachment sites or groups may for example be selected from carboxylic acid, succinimide, benzoic acid such as vinyl benzoic acid, hydroxyl, acrylate, ionisable groups such as acid and base groups and the like. Reactive groups and their combinations are known to those skilled in the art.

Copolymer may be provided in the form of alternating copolymer, block copolymer and may be linear or branched or combinations thereof. Indicator monomer and ionisable group, moiety or monomer may be provided independently at hydrophilic copolymer or prepolymer chain termini, and optionally additionally at a plurality of sites along the polymer backbone.

Ionisable monomer may be provided in any convenient ratio within the hydrophilic copolymer, for example from 1:35, for example 1:5 up to 35:1 ionisable monomer:hydrophilic monomer.

Hydrophilic Monomer

Hydrophilic monomer is preferably selected from acrylamides such as acrylamide, alkyl acrylamide such as ethyl acrylamide, propyl acrylamide or butyl acrylamide and allyl acrylamide; and from acrylate, acrylic acid and the like. The or each hydrophilic monomer may be independently selected from one or a combination of acrylamide, acrylate, acrylic acid and the like.

Ionisable Functional Groups and Monomer

An ionisable functional group or moiety bears charge or is uncharged at different pH. —COOH groups are charged at high pH or low pH or are uncharged at neutral or moderately high pH. Such group or moiety is suitably reversibly ionisable.

Change in pH at a locus, for example from low to high pH or high to low pH causes change in charge of an ionisable group or moiety having pKa in the region of the pH change. In association with hydrophilic monomer, prepolymer and/or copolymer, such change in charge confers change in hydrophilicity. For example for an ionisable moiety comprising COOH the change in hydrophilicity is in the region of pKa 5.

An ionisable group or moiety is selected from acid or base groups and moieties, and from groups or moieties which exhibit a characteristic pKa value in the range 2 to 12 or in the range 5 to 10. pKa may be tailored by choice of a larger chemical entity of which the group or moiety forms part.

Ionisable group or moiety may for example be selected from carboxylic acid, amide such as succinimide, sulfonic acid, benzoic acid such as vinyl benzoic acid, hydroxyl, acrylate, acrylic acid, amine, and the like. Reference to acrylate includes its ionisable counterpart acrylic acid.

Ionisable monomer is suitably selected from polymerisable monomers bearing ionisable functional groups or moieties. Ionisable monomer is preferably selected from acrylic acid such as acrylic acid and methacrylic acid, sulfonic acid such as vinyl sulfonic acid, amino acids, peptides and, hydroxyl acids, and other unsaturated acids and unsaturated bases, for example as hereinbefore defined.

In an embodiment ionisable acrylic monomer may be provided by means of for example acrylic or acrylate hydrophilic adhesives, a number of which incorporate ionisable moieties and their copolymers with other acrylic or vinylic monomers. Ionisable groups or moieties such as OH or COOH may be pendant to the polymer backbone and/or incorporated therein such as by means of ionisable monomers such as 2-hydroxy-ethylmethacrylate.

Acrylates may include high alkyl acrylates such as poly (n-butyl)acrylate, poly(2-ethylhexyl acrylate) and poly(isooctyl acrylate), and multiple component acrylic copolymers including 2-ethylhexyl acrylate (2-EHA), 2-hydroxyethyl acrylate (2-HEA), glycidyl methacrylate (GMA) and vinyl acetate (Vac).

Acrylamides may include copolymers of NIPAAm with acrylic acid monomer or derivative of methacrylate polymer comprising amino acid groups or peptides in side chains such as copolymer gels of methacroyloyl-L-alanine-methyl ester (MA-L-Ala-OMe) and 2-hydroxypropyl methacrylate (HPMA)

In an embodiment hydrophilic ionisable comonomer includes methacrylic acid-co-acrylamide or vinylsulphonic acid-co-acrylamide. In an embodiment hydrophilic ionisable copolymer includes polyacrylic acid-co-acrylamide.

In an embodiment hydrophilic ionisable comonomer or copolymer may comprise amino acids coupled to a hydrophilic copolymer backbone, such as a polyacrylate, polyacrylic acid, polymethacrylic acid or vinyl sulphonic acid backbone via either the amine group or the carboxyl group In this embodiment a series of copolymers or either acids or bases or a combination thereof may be generated. A series of hydrophilic ionisable copolymers of either acids or bases or a combination or copolymer comprising a series of such acid or base or combination provides for tailoring pKa of polyurethane material as hereinbefore defined in convenient manner.

Carboxylic acids are of particular application in the present invention, forming weak polyacids. Examples of carboxylic acids include the acrylic acids, polyacrylic acid (PAAc), polymethacrylic acid (PMAAc), polyethacrylic acid, more particularly poly-2-ethyl acrylic acid (PEAAc), polypropylacrylic acid, more particularly poly-2-propyl acrylic acid (PPAAc).

Polybases include poly (N, N'-dimethyl aminoethyl methacrylate (PDMAEMA) and poly (N, N'-diethyl aminoethyl methacrylate (PDEAEMA), polyvinylpyridines (PVP), more particularly based on 4-vinylpyridine (4VP) or 2-vinylpyridine (2VP), polyvinyl imidazole) (PVI), quaternised polypropylene imine dendrimers, and polymers based on imidazole, dibutylamine and tertiary amine methacrylates.

The pKa of polyacids bearing the carboxylic group is approximately 5-6.

The pKa of succinimide is approximately 9.5.

The pKa of benzoic acid is approximately 7.

The pKa of the polyvinylpyridines is approximately 3.5-4.5.

The pKa of PDEAEMA is approximately 7.5.

Amino acids typically have pKa (—$CO_2H$) in the range 1.5-2.5 and pKa (—$NH_3^+$) in the range 8.7-10.7. Ionisation to form $NH_3^+$ is in the range corresponding to sub-optimal wound health. Illustrative amino acids which may be employed as ionisable group or moiety, and their characteristic pKas are as follows, wherein:

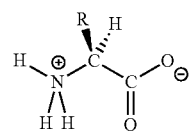

the structure of a generic amino acid is as here illustrated. All of handedness). The form shown (the S-amino acid, or L-amino acid) is the most common form found in plants and animals. The mirror image of each amino acid can be found in nature, although they are less common; and wherein In the table, the third through fifth columns give pKa values of groups: —$NH_3$ refers to the protonated amino group, the $CO_2H$ refers to the carboxylic acid group on the □-carbon, and the side chain is just that. In all cases, these refer to the free amino acid, and not the amino acid incorporated into a polypeptide or protein chain. The $pK_a$ shift on incorporation in a polypeptide or protein may be simply calibrated to a true value, taking into consideration other factors of the copolymer and the network polymer.

| Amino Acid | R | —$NH_3^+$ | —$CO_2H$ | Side chain | pI |
|---|---|---|---|---|---|
| Glycine, Gly | —H | 9.78 | 2.35 | | 5.97 |
| Alanine, Ala | —$CH_3$ | 9.87 | 2.35 | | 6.02 |
| Valine, Val | —$CH(CH_3)_2$ | 9.74 | 2.29 | | 5.97 |
| Leucine, Leu | $CH_2CH(CH_3)2$ | 9.74 | 2.33 | | 5.98 |
| Isoleucine, Ile | $CH(CH_3)CH_2CH_3$ | 9.76 | 2.32 | | 6.02 |
| Phenylalanine, Phe | —$CH_2$—C₆H₅ | 9.31 | 2.20 | | 5.48 |
| Tryptophan, Trp | —$CH_2$—indole | 9.41 | 2.46 | | 5.88 |
| Tyrosine, Tyr | —$CH_2$—C₆H₄—OH | 9.21 | 2.20 | 10.46 | 5.65 |
| Histidine, His | —$CH_2$—imidazole | 9.33 | 1.80 | 6.04* | 7.58 |
| Serine, Ser | $CH_2OH$ | 9.21 | 2.19 | | 5.68 |
| Threonine, Thr | $CH(CH_3)$—OH | 9.10 | 2.09 | | 6.53 |
| Methionine, Met | $CH_2CH_2SCH_3$ | 9.28 | 2.13 | | 5.75 |
| Cysteine, Cys | $CH_2SH$ | 10.70 | 1.92 | 8.37 | 5.14 |
| Aspartic Acid, Asp | $CH_2CO_2H$ | 9.90 | 1.99 | 3.90 | 2.87 |
| Glutamic Acid, Glu | $CH_2CH_2CO_2H$ | 9.47 | 2.10 | 4.07 | 3.22 |

-continued

| Amino Acid | R | —NH$_3^+$ | —CO$_2$H | Side chain | pI |
|---|---|---|---|---|---|
| Asparagine, Asn | CH$_2$CONH$_2$ | 8.72 | 2.14 | | 5.41 |
| Glutamine, Gln | CH$_2$CH$_2$CONH$_2$ | 9.13 | 2.17 | | 5.65 |
| Lysine, Lys | (CH$_2$)$_4$NH$_2$ | 9.06 | 2.16 | 10.54* | 9.74 |
| Arginine, Arg | —(CH$_2$)$_3$—NH—C(=NH)NH$_2$ | 8.99 | 1.82 | 12.48* | 10.76 |
| Proline, Pro | (pyrrolidine-CO$_2^-$, NH) | 10.64 | 1.95 | | 6.10 |

*Refers to the conjugate acid.

Amino acids incorporated as a functional moiety within peptides provide further opportunity to tailor the responsiveness and indication of the material and device of the invention. Illustrative peptides which may be employed as ionisable monomer, and their characteristic pKas are as follows:

Approximate pKa values of ionizable groups of amino acids and peptides (side chains listed unless otherwise noted):
Aspartate (carboxyl): 4
Glutamate (carboxyl): 4
Histidine (imidazole): 6
Cysteine (sulfhydryl): 8.5
Tyrosine (hydroxyl): 10.5
lysine (amino): 10.5
Arginine (guanidino): 12.5
Serine (hydroxyl): 13
Threonine (hydroxyl): 13
☐, carboxyl of free amino acid: 2
☐, amino of free amino acid: 9.5
C, terminal carboxyl of peptide: 3
N, terminal amino of peptide: 8

Amino acids are suitable for coupling to a polyacrylic acid backbone via either the amine group or the carboxyl group. A plurality of pH responsive hydrophilic copolymers may be provided comprising a plurality of amino acids or hydroxyl acids. In the same manner a plurality of copolymers may be generated comprising a plurality of the corresponding bases. Individual acids and bases may be selected for this purpose according to characteristic pKa.

Ionisable groups or moieties may be provided by one or more ionisable monomers. The material may comprise a plurality of ionisable groups or moieties provided on one copolymer or provided on each of a plurality of copolymers. The material may comprise an ionisable comonomer comprising a plurality of ionisable groups or moieties or a plurality of ionisable comonomers each provide one or more ionisable groups or moieties, Ionisable functional group or moiety or monomer are suitably selected from acid and/or base functional groups and moieties and monomers which are sensitive to pH of locus. Ionisable functional group or moiety is suitably ionisable monomer. Ionisable monomer is suitably selected from one or more acid monomers, one or more base monomers, and from a combination of one or more acid monomers and one or more base monomers. Ionisable monomers are suitably sensitive to pH of locus, preferably sensitive to one of favourable and unfavourable pH of locus, preferably undergoing ionisation on transition from one of favourable pH and unfavourable pH to the other of favourable pH and unfavorable pH.

A plurality of ionisable functional groups or monomers may be selected according to characteristic pKa which is indicative of a desired condition at a locus. For example a change in indication signals breakdown of desired condition and thus onset of an undesired condition at a locus. In such case, characteristic pKa corresponds to pH of beneficial wound health, or a transition from beneficial to deteriorating.

Alternatively or additionally a plurality of ionisable functional groups or monomers may be selected according to characteristic pKa which is directly indicative of a non-desired condition at a locus. For example a change in indication directly signals onset of an undesired condition at a locus. In such case, characteristic pKa corresponds to deteriorating or non-beneficial wound health.

Alternatively a plurality of ionisable functional groups or monomers may be selected according to a plurality of characteristic pKas which are indicative of a desired condition at a locus, a non-desired condition at a locus or a combination of desired and non-desired conditions at a locus. For example a change in indication directly signals onset and progression of a desired condition at a locus, onset and progression of an un desired condition at a locus, or a combination thereof. In such case, characteristic pKa corresponds to beneficial wound health in varying degrees of beneficial health, deteriorating or non-beneficial wound health in varying degrees of deteriorating or non-beneficial health, or a combination thereof.

Ionisable moiety or monomer is suitably present in up to 35 moles thereof to 1 mole hydrophilic monomer or prepolymer.

Expressed as a wt:wt ratio, ionisable monomer:hydrophilic monomer or prepolymer may be in the range 3-30:100 wt:wt.

Orientation of ionisable group or moiety or monomer in relation to the copolymer is not insignificant. Hydrophilic copolymer suitably comprises ionisable group or moiety or monomer disposed in pendant manner, for example at branch termini, along the hydrophilic copolymer backbone or at chain termini.

Indicator Monomer

Indicator monomer as hereinbefore defined preferably provides indication or change in indication in the form of an optical change, a molecular or phase change, or a change in adsorption, absorption or emission signal or spectrum in the UV, visible or Infra red regions of the electromagnetic spectrum.

Indicator monomers and the like are known in the art and include those which are sensitive to hydrophilic or polar environments.

Preferably indicator is selected from solvatochromic dyes, including fluorescent dyes, colour changing indicators, and combinations thereof and their polymerisable monomers or oligomers. Solvatochromism is the ability of a chemical substance to change color due to a change in solvent polarity. Preferred indicator includes polymerisable fluorescent solvatochromic dyes, i.e. dyes which may be incorporated as a copolymer with the hydrophilic copolymer and which change fluorescence in response to a change in polarity. Solvatochromic dyes provide a change in maximum absorption and in fluorescence in response to a polar to non-polar transition. Preferred solvatochromic indicator exhibits a wide range of polar sensing.

Preferred indicators include any which are polymerisable or which may be rendered polymerisable and which exhibit fluorescent solvatochromic behaviour.

More preferably indicator monomer is selected from one or more of the naphthalenes, phenoxazines, phenylazenes and phenylazos compounds and their derivatives, for example Dansyl cadavarine (5-amino pentyl)-5-diethylamino-1-napthalene sulphonamide) and reactive derivatives thereof including Dansyl chloride and
N-[2[[[(5-N,N-dimethylamino)-1-naphthalenyl sulphonyl]-amino]ethyl]-2-propenamide (DANSAEP),
Nile Red™ (9-diethylamino-5H-benzo[a]phenoxazine-5-one) 2-[4(2-hydroxyethylsulfonyl)-phenyl]diazenyl)-4-methylphenol,
Nile Blue 5-amino-([9-(diethylamino(benzo[a]phenoxazin-7-ium) sulphonate and polymerisable forms including the corresponding acrylamide, 1-hydroxy-4-[4[(hydroxyethylsulphonyl)-phenylazo]-napthalene-2-sulphonate, 2-fluoro-4-[4[(2-hydroxyethanesulphonyl)-phenylazo]-6-methoxy phenol, 4-[4-12-hydroxyethylsulphonyl)-phenylazo]-2,6-dimethoxyphenol, fluorescent monomers with benzofurazan skeleton, including for example 4-12-acryloyl oxyethylamino)-7-nitro-2,1,3-benzoxadiazole (NBD-AE) and 4-12-acryloylaminoethylamino)-7-nitro-2,1,3-benzodiazole (NBD-AA), 4-amino-1,8 napthalimide derivatives including 2-16-(dimethylamino)-1,3-dioxo-1H-benzo(de)isoquinolin-2(3H)-yl) ethyl methacrylate
and reactive derivatives and combinations thereof.

Reference herein to Nile Red™, includes its reactive derivatives in particular hydroxyl Nile Red™ 9-(diethylamino-2-hydroxy-5H-benzo[a]phenoxazine-5-one and Nile Red™ acrylate 9-(diethylamino-2-acryloyloxy-5H-benzo[a]phenoxazine-5-one. Nile Red is known as a fluorescent indicator for bacteria and intracellular lipids. Nile Red fluoresces in lipid-rich environments. Fluorescence is at different wavelength according to the polarity of the environment, and Nile Red does not fluoresce in most polar solvents. It can be readily visualised using an epifluorescence microscope.

Nile Red™ is commercially available as 9-diethylamino-5H-benzo[a]phenoxazine-5-one. Hydroxyl Nile Red™ may be obtained in known manner or Nile Red acrylate may be obtained by synthesising the hydroxyl derivative of Nile Red and reacting with acryloyl chloride for example as disclosed in Chemistry of Materials 2011, 23, 3348-3356, the contents of which are incorporated herein by reference.

The fluorescence characteristics of Nile Red™ monomer are essentially the same as Nile Red™ as follows Nile red absorbance max in water=584 nm, emission max in water=666 nm Absorbance max in cyclohexane=469 nm, emission max in cyclohexane=570 nm, ref Green Chemistry 2001, 3, 210-215

Nile Blue is commercially available as the 5-amino 9-(diethylamino)benzo[a]phenoxazin-7-ium sulphonate which may conveniently be converted to thecorresponding acrylamide.

Nile blue absorbance max in water=635 nm, emission max in water=674 nm

Absorbance max in chloroform=624 nm, emission max in chloroform=647 nm,

Reference herein to Dansyl™, includes its reactive derivatives in particular Dansyl chloride. Dansyl™ is commercially available as Dansyl™ cadavarine (5-amino pentyl)-5-diethylamino-1-napthalene sulphonamide). Dansyl cadaverine may be reacted with acryloyl chloride to give an acrylamide derivative, or may be provided as N-[2[[[(5-N,N-dimethylamino)-1-naphthalenyl sulphonyl]-amino]ethyl]-2-propenamide (DANSAEP) as disclosed in Chemical Physics Letters 307 (1999) 55-61 the contents of which are incorporated herein by reference.

Dansyl cadaverine is commercially available. Dansyl acrylamide may be obtained in known manner for example as disclosed in Chemical Physics Letters 307 (1999) 55-61, the contents of which are incorporated herein by reference.

Dansyl monomer has fluorescence characteristics including absorbance max in water=329 nm, emission max in water=530 nm, absorbance max in hexane=333.7 nm, emission max in hexane=463 nm.

Fluorescent monomers with benzofurazan skeleton as hereinbefore defined may be obtained in known manner for example as disclosed in Analytical Chemistry 2003, 75, 5926-5935, the contents of which are incorporated herein by reference.

Fluorescent monomers with benzofurazan skeleton may be excited at 469 nm.

NBD-AE emission max in isobutanol 519 nm, emission max in water 535 nm

NBD-AA emission max in isobutanol 521 nm, emission max in water 536 nm 4-amino-1,8 naphthalimide derivatives as hereinbefore defined may be obtained in known manner for example as disclosed in Journal of Materials Chemistry C, 2013, 1, 6603-6612, the contents of which are incorporated herein by reference.

4-amino-1,8 naphthalimide derivatives. When polymerised with NIPAM, have an absorbance max in PBS, 20 C=448 nm, emission maximum in PBS, 20 C=544 nm, absorbance max in chloroform=422 nm, emission maximum in chloroform=513 nm.

Preferred indicator has a narrow emission range, more preferably narrow excitation and emission ranges for example in a range of 5 up to 100 nm, more preferably 5 up to 50 nm, most preferably 2-20 nm.

Change in indication of indicator monomer is suitably reversible.

Indicator may be present in an amount defined as molar ratio of hydrophilic copolymer:indicator monomer of >50:1, preferably 1000-2500:1, for example 1500-2200:1. Indicator present in such relatively low amounts provides the required sensitivity and moreover provides superior indication, Preferably indicator monomer is provided as wt/wt ratio with hydrophilic monomer of 3-30:100 indicator monomer:hydrophilic monomer Indicating Scale Fluorescence characteristics of Nile Red in different solvents are well known and commonly presented as a scale of colours or spectrum of colors.

In similar manner indicator monomer is suitably calibrated according to a scale or spectrum representing copolymer hydrophilicity at characteristic pHs or pKas. Calibration is suitably refined to allow for any effect of network polymer, ionisable monomer and the like.

Material or device comprising Nile Red indicator monomer therefore provides a range or spectrum of colours ranging through purple, pink, orange, yellow, green and varying intensities. Indication may be in visible or ultraviolet spectrum.

Microbes

Microbe which may be detected by pH are selected from Gram positive bacteria for example selected from *Staphylococcus* such as *Staph. aureus*, *Staph. epidermidis* and MRSA, *Streptococcus, Enterococcus, Corynebacterium* and *Clostridium* such as *C. difficile*, also *Peptostreptococcus, Lactobacillus, Propionibacterium, Bifidobacterium* and *Actinomyces*;

Gram negative bacteria for example selected from proteobacteria such as Enterobacteriaceae for example, *Escherichia coli, Salmonella, Shigella, Pseudomonas* such as *Pseudomonas aeruginosa, Proteus, Klebsiella*, also *Legionella, Hemophilus, Neisseria, Acinetobacter* such as *A. baumannii, Bacteroides, Prevotella, Fusobacterium, Porphyromonas* and the cyanobacteria and spirochaetes.

Microbes typically encountered in a wound environment include for example Gram negative aerobic bacteria such as *Pseudomonas aeruginosa*, Gram positive bacteria such as *Staphylococcus aureus*, more particularly MRSA (methicillin resistant *Staphylococcus aureus*) also known as ORSA (oxacilin resistant *Staphylococcus aureus*) anaerobic bacteria such as *Bacteroides fragilis*, yeast such as *Candida albicans* and fungi such as *Aspergillis braziliansis*.

Microbes may be detected at a level of bioburden including any of contaminated, colonised, critically colonised and infection level. These levels are given the meaning known in the art.

Use

The device as hereinbefore defined may be for any use in which indication of pH, more preferably detection or sensing of microbes by means of indication of pH is desired.

Suitably the device is for use in applications selected from medical, dental, hygiene, point of use sterilisation, sanitation, personal care, biosurveillance and packaging. Use may be for purpose of quality control or point of care monitoring.

Such uses include for example the management of wounds, hygiene and sterilisation of articles including medical and dental articles, hygiene and sterilisation of food or of fluids, including water and air, or systems for their preparation and generation such as food preparation or packaging plants, ventilation systems, water management systems, and in particular such uses for which the detection or binding of bacteria, monitoring of pH, and the like is beneficial.

The device may be in desired form suitable for the intended use, for example sheet form. Suitably the device is in the form of a block, sheet, film, membrane, layer or coating, fiber, woven or non-woven being foamed or non foamed, in particular being conformable foam block or sheet, film, membrane, woven or non-woven or layer is particularly envisaged as hereinabove described.

In a preferred embodiment the device is for use as a wound dressing or part thereof, for interrogating biological fluids including wound fluid, serum, urine, as a medical or dental sponge or wipe or the like, or pH probe or sensor in such applications or independent applications.

Material or device for use as a wound dressing or part thereof or in interrogating biological fluids includes use for interrogating wound fluid, for example may be in form of a dipstick, lining for vacuum line or wound fluid conduit, collar for wound fluid conduit port, wound fluid filter, wound filler or top film for wound filler and the like, in particular in relation to negative pressure wound therapy (NPWT), collar for port in other applications providing at the port a moist locus or environment as hereinbefore defined, and the like.

Preferably the device comprises a wound dressing or is for use as a secondary or primary dressing in conjunction with a primary or secondary wound dressing. As a primary dressing the device may be in the form of a wound contact layer or wound filler for an absorbent, odour absorbing or like secondary dressing, for example in moist wound healing. As a secondary dressing the device may be in the form of a fluid absorption or odour absorption layer supplementary to that of a primary dressing or be in the form of a top film to retain a primary dressing in place. Such decision may be the clinician's choice. pH or presence of bacteria may be assessed upon application of and removal of the device as primary dressing from the wound. The device may be intended for positioning at or near a lower surface of a secondary dressing. The device may be the wound contacting layer for the secondary dressing. The device may be for use as a cover layer, or intermediate layer for a primary dressing In management of deep or chronic wounds, the device may be placed into the wound to detect bacteria or pH and removed from the wound intact. Foam for use with negative pressure wound dressing is particularly contemplated.

Devices may be used to detect pH or bacteria remote from the wound. For example polyurethane material may be provided in the form of a polyurethane film or polyurethane foam plug for insertion in the vacuum line of a NPWT device, for example at the entrance to a port provided on a NPWT dressing. A device is thereby configured to contact wound fluid emanating from a wound bed to be drawn off via a vacuum line. Such wound fluid may thereby be caused to flow over or through the device. The device may thereby provide indication of species or stimulus in relation to the fluid.

A device may be provided in the form of a polyurethane film for use under the drape of a NPWT dressing located over a filler material. Polyurethane material is thereby configured to contact wound fluid comprised within the filler material as a reservoir of fluid for removal via a vacuum line. The device may thereby provide indication of species or stimulus in relation to the fluid.

A device may be provided in the form of a polyurethane foam for use as a dip-stick or swab. The device is thereby configured to contact wound fluid comprised in a wound locus by contact with the wound surface. The device may thereby provide indication of species or stimulus in relation to the fluid.

Accordingly a device for use as a wound dressing or part thereof or in interrogating biological fluids includes use for interrogating wound fluid, for example may be in form of a dipstick, lining or plug for vacuum line or wound fluid conduit, collar for wound fluid conduit port, wound fluid filter, wound filler or top film for wound filler and the like, in particular in relation to negative pressure wound therapy, collar for port in connection with a fluid environment and the like.

The material or device may be provided in shape or size or a range of shapes or sizes suitable for use on a wound or at a locus, or may be cut to size or shape.

Preferably the device is manufactured with use of a block or sheet, film or membrane cut to size and shape in the manufacture of a device for use as hereinbefore defined for example as a wound dressing or part thereof or for use in interrogating wound fluid or other uses as hereinbefore defined.

In a further aspect there is provided a device as hereinbefore defined in the form of a monolith such as a block, sheet or roll, of polyurethane material defined by external surface(s) and a solid or porous internal cross section comprising hydrophilic copolymer distributed at external surface(s) and throughout the cross section thereof, said monolith being adapted for sizing and shaping without macroscopic change in bulk distribution of hydrophilic copolymer within and throughout the monolith.

In a particular advantage the hydrophilic copolymer provides indicator and ionisable function distributed throughout the polyurethane network, and thereby provided at any face of a device even when manufactured from material cut to size or shape. This is a particular advantage when compared to devices having bacterial or pH sensing function applied as a coating at a surface, and which are not active at a face exposed by cutting after coating.

The device may be for use in treating wounds which are contaminated by or susceptible to contamination by microbes as hereinbefore defined. A particularly useful application is in treating wounds contaminated by or susceptible to contamination by bacteria, yeast and/or fungi.

Wound management includes management of chronic and acute, full thickness, partial thickness, and shallow granulating exuding wounds. Wounds for which the hereinbefore defined material has particular use include for example ulcers and pressure sores such as leg ulcers; pressure ulcers; diabetic ulcers; surgical wounds; traumatic wounds; donor sites; burns such as partial thickness burns; tunneling and fistulae wounds; wounds left to heal by secondary intent; and wounds that are prone to bleeding such as wounds that have been surgically or mechanically debrided, cavity wounds, sinus and open wounds.

Method for Manufacture of Device

In a further aspect the invention comprises a method for the manufacture of a device as hereinbefore defined comprising generating a surface configured to contact a locus as hereinbefore defined wherein the surface comprises a polyurethane material as hereinbefore defined.

The method may comprise cutting a sheet of polyurethane material to size or shape to generate a surface as hereinbefore defined. Alternatively the method comprises providing a surface and providing a polyurethane material as hereinbefore defined applied to a face thereof configured to contact a locus, or to an opposing face thereof.

Preferably the method comprises sterilisation in known manner.

Construct

In a further aspect the invention comprises a construct comprising a device as hereinbefore defined fabricated together with additional components. A construct may comprise a surface as hereinbefore defined provided in a device as hereinbefore defined together with one or more layers of functional material as a laminar device. Layers may be coextensive with the surface or device or otherwise, for example may comprise a strip or zone superimposed on the surface or the device or a part thereof.

A strip or zone may comprise a reference strip providing reference information for processing information relating to indication and change in indication and generating output information relating to bacteria or pH.

A reference strip may comprise information relating to wavelength, and may further comprise a temperature sensor. Wavelength and/or temperature information may be used in calibrating the construct.

A strip or zone or layer may comprise a display such as a VDU, preferably a flexible VDU such as a polymeric VDU for displaying reference information, information relating to indication or change in indication, or output information derived by processing thereof.

Layers of functional material may include one or more layers of perforated film or mesh, fluid-impermeable film, superabsorbent material and/or fluid distributing material and obscuring material.

Such layer may be of size and shape corresponding to the conventional equivalent.

Alternatively such layer may extend across only one or more parts or zones of the construct. For example a foam layer may be of part thickness and may be positioned in laminar manner with a corresponding conventional layer of reduced thickness. A wound contact layer may comprise an adhesive layer of polyurethane material as herein defined such as a xerogel as herein defined optionally applied to a conventional film. A fluid impermeable film may optionally be provided and comprise polyurethane material as herein defined, applied as a film in conventional manner.

In a further aspect there is provided a method for manufacturing a construct as hereinbefore defined comprising providing a device or sheet of conformable polyurethane material as hereinbefore defined in desired shape and size, and optionally providing together with one or more layers of functional material as a laminar device, preferably together with one or more layers of perforated film, fluid-impermeable film, superabsorbent material and/or fluid distributing material. The method may comprise positioning an obscuring layer optionally comprising one or more windows to facilitate inspection or interrogation of the construct.

Wound Dressing

In a further aspect the invention comprises a wound dressing comprising
(a) a wound contacting surface or layer
(b) an opposing non-wound contacting surface or layer
(c) an optional wound exudate absorbing layer comprised between (a) and (c)
wherein (a) and/or (b) and/or (c) comprises polyurethane material or a device or construct as hereinbefore defined which material or device or construct comprises a polyurethane polymer network having a hydrophilic copolymer immobilised therein
wherein the hydrophilic copolymer comprises ionisable moieties or monomer and indicator monomer wherein indicator monomer provides a first indication prior to contact with the wound and changes indication as a function of pH at the wound.

The wound dressing may comprise any features of the device as herein described.

Preferably a wound dressing comprises (a) conformable elastomeric apertured film, (c) an intermediate conformable hydrophilic foam layer, and (b) a continuous moisture vapour transmitting conformable polymer film outer layer in which the layers are attached in a contiguous and co-extensive relationship. In this embodiment a device or wound dressing may comprise a modification of commercially available absorbent foam, woven or non-woven fiber or mesh, film or membrane, or wound dressing comprising absorbent foam, woven or non-woven fiber or mesh, film or membrane such as polyurethane foam. Polyurethane foams or polyurethane foam dressings which might beneficially incorporate the polyurethane material as hereinbefore defined include ALLEVYN™ foam, ALLEVYN™ Adhesive, ALLEVYN™ Gentle Border, ALLEVYN™ Gentle, ALLEVYN™ Ag Gentle Border, ALLEVYN™ Ag Gentle, PICO™ and other commercially available absorbent, hydrophilic polyurethane foams based on polyurethane polyol moieties, most particularly being compatible with the method of generating the polyurethane material as hereinbefore defined.

FIG. 3.1 depicts a construct or device 100 having a) a wound-contacting surface 102 and c) an opposing non-wound-contacting surface 104. FIG. 3.2 depicts the construct or device 100 in situ on a wound 106. The construct or device 100 can be made of any material that is suitable for contact with the wound. Wound contact layers are known in the art and include the PROFORE wound contact non-adherent dressing (Smith and Nephew, Inc), the MEPITEL Soft Silicone Wound Contact Layer (MOlnlycke Health Care US, LLC), CUTICERIN, a low-adherent acetate gauze (Smith and Nephew, Inc) and the DRYNET Wound Veil (Smith and Nephew, Inc).

Preferably a wound contact layer is characterised by being a conformable, transparent, non-adherent porous sheet for placing on or in an open wound bed to protect the tissue from direct contact with other agents or dressings applied to the wound.

Preferably a wound contact layer is porous to allow wound exudate to pass through for absorption by an overlying, secondary dressing. Construct or Device 100 may be porous and can be a made of a non-woven, a perforated film or a mesh. Alternatively, in applications in which the construct or device 100 is to be transiently placed into the wound 50 to detect pH or microbes between dressing changes, the construct or device 100 may be non-porous.

Preferably a wound contacting surface 102 surface comprises a border region for sealing to skin about the wound.

A non-wound contacting surface 104 may comprise an obscuring layer. Alternatively a non wound contacting surface 104 or part thereof may be transparent to permit inspection of the wound contacting surface 102, for example may comprise a window or aperture in the obscuring layer or a plurality of windows or apertures.

The construct or device further includes a polyurethane material as hereinbefore defined 108 which comprises or is applied as layer to one or both of surfaces 102 (shown in FIG. 3.1) and/or 104 orc) intermediate therebetween or which comprises device 100.

Suitably the material is provided as a sheet or layer so that it is not washed away by the wound exudate.

In embodiments on which the polyurethane material comprises only one surface a) or c) of a non-porous construct or device, then an indication, for indicating which side the material is comprised on may be provided. This indication allows the user to appropriately orient the construct or device during placement on or in a wound to ensure that the correct surface provides the wound-contacting surface.

The polyurethane material may be applied across substantially the entire surface 102 and/or 104, to allow the detection across the entire wound bed to be mapped. Alternatively, the polyurethane material may be applied to discrete zones of surfaces 102 and/or 104.

The device may include further orientation marks and optional reference marks to assist in reading the device and identifying, recording and monitoring results. The device may additionally comprise elements of a construct as hereinbefore defined.

The device is further illustrated in FIG. 3.2.1-3.2.3 in the form of a dressing in which FIG. 3.2.1 illustrates layers a) to c) as hereinbefore defined, the polyurethane material provided as layer c), clearly visible as having pink coloration; FIG. 3.2.2 illustrates layers a) to c) as hereinbefore defined, in side elevation view with additional obscuring layer, below which the polyurethane material provided as layer c) is masked, and is visible at the edges only; and FIG. 3.2.3 illustrates the variant of FIG. 3.2.2 in plan view.

The invention is of particular application in providing a microbe responsive pH sensor or wound dressing comprising pH-responsive polyurethane foam material as hereinbefore defined.

In a further aspect there is provided a method for manufacturing a wound dressing as hereinbefore defined comprising providing a sheet of conformable polyurethane material in desired shape and size, and optionally providing together with one or more layers of functional material as a laminar device, preferably together with one or more layers of perforated film, fluid-impermeable film, superabsorbent material and/or fluid distributing material, obscuring material and the like.

Suitably in the manufacture of a device the wound contacting surface and overlying fluid-impermeable membrane have a surface area which is greater than that of an intermediate layers.

Device or polyurethane material as hereinbefore defined may be sterile, and more particularly terminally sterile, as known in the art. Preferably such device or material is provided within sterilised primary packaging. Suitably the method includes optional sterilisation in known manner and packaging. Sterilisation is suitably for example by radiation such as gamma or ebeam radiation, or by thermal sterilisation.

In a particular advantage we have found that the materials and device may be provided in sterile or terminally sterile form, without deleterious effect thereon.

Suitably the method is a method for manufacture of a laminar wound dressing, for example an ALLEVYN or PICO dressing as hereinbefore defined or as known in the art.

Kit

In a further aspect there is provided a kit comprising at least one device as hereinbefore defined, the kit further comprising a reference strip providing reference information for processing information relating to indication and change in indication and generating output information relating to bacteria or pH.

Preferably a reference strip provides information to calibrate the device. For example a references strip will calibrate the device to pick up the desired wavelength of fluorescence emission and correct as necessary for processing acquired wavelength information.

A reference strip may alternatively be provided integral with material or a device or dressing as herein defined.

The device may be intended for visual inspection or inspection with use of a suitable inspection or scanning device or reader.

Inspecting or Scanning Device or Reader (Interfacing Device)

In a further aspect of the invention there is provided an inspection or scanning device or reader for example for inspecting or scanning or reading a pH sensing and/or detecting device, for example a device as hereinbefore defined, receiving information relating to indication or change in indication and providing output information relating to microbes or pH present at a locus, the scanning device comprising
interrogation means for acquiring indicating information; a processor for processing indicating information and generating output information,
and a display or connectivity for a display for displaying output information.

Preferably the device or reader comprises interrogation means for acquiring indicating information which comprises color and/or intensity readings indicating pH by means of hydrophilic state of pH indicating hydrophilic polymer material, for example material as hereinbefore defined.

Interrogation means herein may conveniently be described as a sensor or detector, and preferably comprises a light sensor. Light sensors are known in the art and include for example charge coupled devices (CCDs) and active pixel sensors in complementary metal-oxide semiconductors (CMOS).

Interrogation means or sensor or detector may further comprise recording means such as a camera.

Interrogation means or sensor or detector is suitable for the indicating information to be acquired.

In the case that indicating information is a fluorescence signal, interrogation means or sensor or detector may additionally comprise an excitation light source. An excitation light source has the purpose of providing excitation light to fluorescent indicating means for the generation of fluorescence information, such as fluorescence emission in the form of a fluorescence reading or fluorescence signal as hereinbefore defined.

An emission filter may further be provided, suitably for the purpose of eliminating excitation light. Emission filters are known in the art of observing fluorescence. Preferably an emission filter allows passage of light in a narrow bandwidth of for example 635-660 nm, around a central wavelength for example 647 nm.

A fluorescence chamber may additionally be provided for the purpose of containing the excitation light source and an emission filter if present. A fluorescence chamber provides a controlled lighting environment for delivery of excitation light to the sensing device, receipt of emission light therefrom and control of ambient light. Preferably the fluorescence chamber excludes ambient light which might obscure excitation and emission light. The fluorescence chamber may be separate or integral with the interfacing device, a separate chamber for example may comprise a housing to receive material or device to be read.

A fluorescence chamber may be a closed chamber adapted to receive the material or comprise a skirt adapted to be located over the material Preferably a skirt is conformable or flexible. A conformable or flexible skirt may be located over material in situ at a locus and conform to the profile of the material and/or locus to exclude ambient light. In the case of wound management, a locus may be a body part of irregular shape.

A fluorescence chamber may be disposable for single use, or is adapted to be cleaned and/or sterilised for reuse. Suitably the inspection or scanning device or reader is provided in parts allowing disposal or cleaning and/or sterilising of fluorescence chamber.

A light source may be selected from one or more lasers, LEDs and the like. Light sources may emit light at same or different wavelengths. A light source may be associated with one or more filters allowing the desired wavelength emission.

A light source may comprise a light source for emission of broad spectrum light, together with an emission filter for selection of a desired wavelength excitation light, or may comprise one or more light sources for emission of a narrow bandwidth light, such as a specific narrow bandwidth light or a narrow bandwidth of a desired wavelength. For example a light source may comprise one or more LEDs emitting light in a narrow bandwidth around a central wavelength.

Preferably a light source emits light at a wavelength corresponding to the excitation wavelength of the indicating means. A suitable wavelength may be for example in the range 590 nm. Preferably the light source emits light in a narrow bandwidth of for example 580-600 nm around a central wavelength for example 590 nm.

A processor includes means to receive acquired indicating information, means to access software for processing acquired information and means to output processed information.

Means to receive acquired indicating information may comprise a wireless or wired connection. Means to access software may comprise an integral or external memory programmed with software, or internet access to remote software or a combination 50 thereof.

A display may be an optical or digital display. A display suitably provides processed output information in optical or digital format. Preferably a display is a visual display unit for displaying digital images, digital quantitative read out or digital text. Text may for example include instructions to the user such as "infected", "take action", "see specialist" or the like.

Conveniently a display is a display comprised in a camera which combines light detector and display in a single unit.

A display may be integral with or remote and separate from the inspection or scanning device or reader. For example the scanning device or reader may be a mobile phone or other hand held with integral display adapted to be received within the fluorescence chamber. Alternatively or additionally a display is a remote display, for example the device may provide output information to a remote display, and may comprise means to transmit output information for display. In the case of a remote display, the device comprises connectivity for a remote display, for example a socket for a wired communication cable, a socket for a communications mounting or cradle, or wireless connection means such as Bluetooth, telecoms systems, wifi or other suitable means. A remote display may comprise one or more of a VDU, TV console (optionally wall mounted), printer, a component of the material or a construct comprising the material and the like. Variants are innumerable and well known in the art of visual displays, computing and telecommunications.

Preferably an interfacing device is mobile, more preferably is hand held.

Conveniently a mobile hand held interfacing device comprises a smart phone optionally together with an excitation light source and fluorescence chamber as hereinbefore defined. Software may be provided in the form of an App whereby external software access is not required. The App may capture and process an image of the indicating information such as emission fluorescence.

The inspection and/or scanning device or reader may comprise means such as a dock, panel or slot to receive the detection and/or sensing device and directly download information relating to indication or change in indication therefrom.

Processed output information may be in the form of a map, such as a map of fluorescence intensity or a "heat map", optionally calibrated against a fluorescence intensity reference or control.

Processed output information optionally includes location and/or orientation information, subject information for example patient information, date and the like. Processed output information may be overlaid on or otherwise compared with processed output information relating to the same or different locus.

In a further aspect there is provided a kit comprising two or more components of an inspection or scanning device or reader as hereinbefore defined, for example interrogation means and fluorescence chamber.

In a further aspect there is provided a method for inspecting or scanning or reading a sensing and/or detecting device as hereinbefore defined comprising
locating an inspection and/or scanning device or reader as hereinbefore defined in relation to the pH sensing device, activating the inspection and or scanning device to
interrogate the detection and/or sensing device and
acquire indicating information for processing, optionally additionally to process indicating information, and optionally additionally to
record or store, display or transmit for display output information.

The method suitably includes classifying output information as an assessment of wound health.

Regular measurement of wound pH can be used (in conjunction with other clinical signs and symptoms) to monitor a healthy wound or flag up a problem prompting further investigation and/or re-evaluation of therapy.

Chronic wounds are typically more alkaline than acute wounds. pH remains alkaline in static, non-healing or infected chronic wounds but in healthy chronic wounds pH steadily falls as healing and re-epithelialisation progresses and the skin's normal acid mantle is reinstated. This phenomenon is supported by an underlying biological rationale, for example, acidity favours healing in chronic and acute wounds by boosting oxygen delivery and cell proliferation, supressing bacterial growth and inhibiting proteolytic enzyme activity. Alkalinity is increased in the presence of bacterial metabolites such as ammonia and Proteolytic enzyme activity peaks around pH8 promoting wound chronicity.

An assessment may be generally classified as deteriorating, stable or improving.

Processed information may be further classified for example as an assessment of localised wound health. An assessment may be generally classified as localised, moderate or extensive health status.

The method may further comprise determining a treatment plan based on the monitoring or assessment. Treatment may include for example continuing current treatment, increasing current treatment, changing treatment or seek further information on wound health.

A method is illustrated for example in the flow scheme of FIG. 4 herein.

In the flow scheme is illustrated an example of "use of device as indicator on wounds" e.g. clinician decisions resulting from different responses which might be detected.

Method for Detecting or Sensing

In a further aspect there is provided a method for detecting or sensing microbes or pH at a locus comprising applying a device comprising material as hereinbefore defined to the locus and interrogating the material or device to obtain an indication indicating detection or sensing of microbes or pH, and optionally additionally monitoring for an indication or change in indication.

Interrogating or monitoring may comprise interrogating or monitoring the material or device directly, for example by means of the indicator.

Alternatively interrogating or monitoring comprises interrogating or monitoring of the device or material indirectly by means of an optical or digital reading or signal in a device for scanning or interfacing with or inspection of the device or material, for example with the indicator.

Method of Treatment

In a further aspect there is provided a method for detecting or monitoring pH in relation to a subject or locus comprising applying a device comprising polyurethane material as hereinbefore defined to the subject or locus and detecting or sensing an indication or change in indication as hereinbefore defined.

Monitoring may comprise monitoring the device comprising polyurethane material directly, for example by means of the indicator.

Alternatively monitoring comprises monitoring of the device comprising polyurethane material indirectly by means of an optical or digital reading or signal in a device for scanning or interfacing with the material, for example with the indicator.

Preferably the method is a method for detecting microbes in or in relation to a subject or locus, comprising applying a device comprising polyurethane material as hereinbefore defined to the subject or locus and monitoring for change in indication.

In a further aspect there is provided a method for treatment of a subject in need thereof comprising applying a device comprising polyurethane material as hereinbefore defined to the subject and monitoring for change in indication.

Preferably the method is for treatment of a wound in a subject in need thereof, wherein the wound is susceptible to microbial contamination or is suspected of being microbially contaminated.

Suitably the method includes interrogating, inspecting or scanning the device comprising polyurethane material to determine binding or proximity of bacteria.

Process for Preparation

Preparation of Polyurethane Material

There is provided a process for the preparation of polyurethane material as hereinbefore defined comprising generating a polyurethane network in the presence of hydrophilic copolymer as hereinbefore defined. Generating a network is suitably by means of cross linking and/or chain extension or the like.

Hydrophilic copolymer may be present during generation of the entire network or part thereof. Preferably the process comprises admixing hydrophilic copolymer together with polyurethane prepolymer or precursors, further together with an amount of networking agent, such as chain extending agent and/or cross linking agent.

The polyurethane network is suitably generated by reaction of isocyanate terminated monomer and long chain diol and/or polyol, directly, or by chain extension and networking reaction of polyurethane prepolymers thereof provided as an intermediate isolated product thereof.

Networking agent may be introduced prior to, simultaneously with or subsequent to reaction of prepolymers.

Polyurethane prepolymer is commercially available as one of the series of HYPOL® Hydrophilic Polyurethane Prepolymer products (W R Grace & Co, Dow Chemical Co).

HYPOL® products are unique reactive liquids characterized by high hydrophilicity and are suitable for the manufacture of foams, gels, coatings and elastomers. Preferred commercially available HYPOL® Polyurethane Prepolymers comprise aromatic polyisocyanate (such as TDI or MDI) or aliphatic polyisocyanate (such as hydrogenated MDI or HDI).

HYPOL® products are capable of holding up to twenty times their weight in liquid. Hydrophilic copolymer may therefore be readily incorporated in an amount of up to twenty times the weight of liquid HYPOL® and form an integral part of the product polyurethane material.

It is one benefit of the invention that hydrophilic copolymer may be simply blended with the combined polyurethane prepolymer and its reagents or precursors during the reaction thereof and/or during chain extension or crosslinking, whereby it is immobilised within the polyurethane network. Hydrophilic copolymer may be blended with one thereof prior to combining. For example hydrophilic copolymer may be combined with an isocyanate component or polyol component or both such as the HYPOL® phase or the aqueous phase for reaction therewith, in a polyurethane system.

The process may comprise introducing a plurality of hydrophilic copolymers as hereinbefore defined simultaneously, for example as a blend, or separately.

Preferably the hydrophilic copolymer or part or an amount thereof is provided in fluid phase, preferably dissolved in suitable solvent or solvated by a component of the reaction to generate polyurethane. Hydrophilic copolymer may be introduced in fluid phase or may adopt fluid phase in situ. Hydrophilic copolymer or an amount thereof present in part or fully dissolved or solvated form is able to integrate within the polyurethane network. Integration may be by means of an interpenetrating or entangled network comprising the polyurethane network polymer and hydrophilic copolymer.

Alternatively hydrophilic copolymer is provided in solid phase such as in powder form for intimate mixing in a polyurethane reaction component, such as the isocyanate, a diol/polyol component, or prepolymer generated therefrom, for example a HYPOL® component, or aqueous phase for use therewith, optionally together with an amount of added solvent for the hydrophilic copolymer. Intimate mixing into a non-aqueous component may be conducted with simultaneous or subsequent addition of an aqueous component. Hydrophilic copolymer or part or an amount thereof is thereby dissolved in the reaction component. Intimate mixing moreover provides hydrophilic copolymer distributed throughout the resulting polyurethane material.

Suitably the hydrophilic copolymer is combined with one or more polyurethane components prior to extrusion or casting of the combined polyurethane reaction components. Casting may be into a mould or onto a surface as known in the art. Extrusion or casting is suitably in manner to form a foamed or non foamed block or sheet, gel, membrane or film, or string, ribbon, thread or like fiber form.

The process may be a process for preparing a foam, xerogel, film or other non-foamed material as hereinbefore defined. Polyurethane material may be cast, such as cast from solvent, or extruded into the above forms as known in the art.

The reaction may be aqueous or non-aqueous. Preferably there is a balance between a low water content suitable for gel or foam formation, to preserve the immobilisation of hydrophilic copolymer and the presence of water to assist in dissolving hydrophilic copolymer and enable network interpenetration or entanglement.

The reaction may conveniently be illustrated in non-limiting manner as follows in Scheme a1:

Scheme a1

Polyurethane material is obtained by step growth polymerisation or chain extension of diisocyanate and diol/polyol or prepolymers thereof as hereinbefore defined in the presence of hydrophilic copolymer copoly (I) as hereinbelow defined:

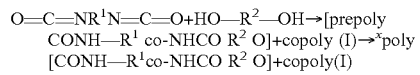

wherein $R^1$ is aromatic hydrocarbyl for example selected from toluene, methylenediphenyl, paraphenylene and naphthyl;

$R^2$ is selected from alkyl, polyester, polycaprolactone, polyether and polycarbonate

*=copoly (I) and x=crosslinker or chain extender as hereinbefore or hereinbelow defined.

Scheme a1 may be conducted as two separate steps or as a single step in which crosslinker or chain extender x is present throughout.

Polymerisation may be performed using any suitable method for example solution, suspension, emulsion and bulk polymerisation methods may all be used.

The process suitably comprises blending, optionally casting or extruding, optionally foaming, and curing as required. Preferably curing is initiated by mixing of polyurethane precursor or prepolymer and hydrophilic copolymer components.

Contacting may be in the presence of optional initiator, catalyst, blowing agent or foaming agent, surfactant, chain extender, cross-linker and the like as known in the art.

The polyurethane foam is suitably generated with the use of surfactants to regulate cell size and prevent collapse.

Where it is desired to prepare a foam, the process may generate foaming agent in situ.

Alternatively or additionally foaming agent may be added. In situ generated foaming agent includes $CO_2$ gas generated from reaction of water and isocyanate. Added foaming agent includes $N_2$ gas and volatile liquids such as HFC-245fa (1,1,3,3-pentafluoropropane) and HFC-134a (1,1,1,2-tetrafluoroethane), and hydrocarbons such as n-pentane and the like.

Chain extenders (f=2) and cross-linkers (f=3 or greater) are suitably selected from low molecular weight hydroxyl and amine terminated compounds, as known in the art. Crosslinking agent may be selected from cross linking agents used in the preparation of foams, such as water or the like.

Polyol is commercially available in a resin or blend incorporating catalyst, surfactant, chain extender and/or cross-linker.

The process may be conducted at ambient temperature or at elevated temperature if it is desired to increase the rate of chain transfer. Preferably the process is conducted at ambient temperature up to 40 C. Elevated temperature is suitably in the range in excess of 100 C, preferably from 125 to 175 C.

The product polyurethane material, is suitably isolated from reaction medium without need for further working up. If desired however the process may optionally include in a further step washing or extraction in an aqueous solvent for the polymer, to remove residual non immobilised polymer. This may be useful in the case that hydrophilic copolymer is present in a wide diversity of molecular weight, branching functionalisation or the like, whereby some polymer is entrained but is not immobilised. Preferably washing or extraction is with any solvent for the hydrophilic copolymer, preferably selected from ethanol, aqueous ethanol, $CH_2Cl_2$, acetone and DMSO. Known techniques may be employed such as a series of solvent bath, nip roller and oven. Preferred solvent is aqueous ethanol. Drying may be in excess of ambient temperature for example about 60 C.

Suitably the process comprises in a previous step the preparation of hydrophilic copolymer as hereinbefore defined.

Preparation of Hydrophilic Copolymer.

Hydrophilic copolymer comprising hydrophilic monomer and ionisable monomers or moieties or groups as hereinbefore defined is commercially available or may be prepared by methods as known in the art. Indicator monomer may be incorporated by techniques as known in the art, with such commercially available copolymer.

For example hydrophilic ionisable copolymers are commercially available such as polyacrylic acid-co-acrylamide (Aldrich).

Hydrophilic acrylic-based adhesive formulations are commercially available, incorporating ionisable monomer such as acrylic acid. For example Smith & Nephew A8 and K 5 adhesives. Ionisable groups or moieties such as OH or COOH are pendant to the polymer backbone and/or are incorporated therein such as by means of ionisable monomers such as 2-hydroxy-ethylmethacrylate.

Acrylic PSAs are homopolymers of acrylic esters and their copolymers with other various acrylic or vinylic monomers. Known systems employ high alkyl acrylates such as poly(n-butyl acrylate), poly(2-ethylhexyl acrylate), and poly (isooctyl acrylate). Their synthesis is referenced in "Synthesis and Optimization of a Four-component Acrylic-based Copolymer as Pressure Sensitive Adhesive", Taghizadeh and Ghasemi, Iranian Polymer Journal 19 (5), 2010, 343-352, which moreover discloses solution copolymerisation of multiple component acrylic copolymers including 2-ethylhexylacrylate (2-EHA), 2-hydroxyethyl acrylate (2-HEA), glycidyl methacrylate (GMA) and vinyl acetate (VAc), using 2,2'-azobisisobutyronitrile (AIBN) as an initiator.

Alternatively amino acids may be coupled to a hydrophilic copolymer backbone, such as a polyacrylate, polyacrylic acid, polymethacrylic acid or vinyl sulphonic acid backbone via either the amine group or the carboxyl group. By this means one or a series of copolymers of either acids or bases may be generated.

Gels Handbook Vol 1 The Fundamentals, Academic Press USA 2001 Osada and Kajiwara (International Standard Book Number: 0-12-394961-0) discloses synthesis of copolymers of acrylamide such as NIPAAm with acrylic acid monomer or derivatives of methacrylate polymer comprising amino acid groups or peptides in side chains such as copolymer gels of methacryloyl-L-alanine-methyl ester (MA-L-ALaOMe) and 2-hydroxypropyl methacrylate (HPMA) [see in particular references 22, 23 therein].

Incorporation of indicator monomer is by conventional techniques as known for example by analogy with PCT/EP2015/065227 published as WO2016/012219 and 065234 published as WO2016/005288 the contents of which are incorporated herein by reference.

For example Nile Red may be copolymerised with these copolymers.

Alternatively hydrophilic copolymer as hereinbefore defined may be obtained by polymerisation of indicator monomer with hydrophilic monomer and ionisable monomer.

For example acrylate monomer such as butyl acrylate and/or 2-ethyl hexyl acrylate with acrylic acid, for example in an amount of 5 wt % or more, in solvent such as acetone may be polymerised with use of suitable initiator such as t-butyl peroxydicarbonate, in the presence of polymerisable indicator monomer such as Nile red acrylate, for example at 0.1-0.5%.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

The invention is now illustrated in non-limiting manner by the following Examples and Figures.

EXAMPLES

1. Hydrophilic copolymer was polymerised incorporating dye (Nile Red, dansyl etc.) label along the copolymer chain.
2. Hydrophilic copolymer was then mixed in with polyurethane prepolymer (polyol and isocyanate or prepolymer thereof) under step growth or chain extension polymerisation conditions with foaming.
3. In subsequent extraction studies, determination can be made of whether hydrophilic copolymer may be extracted from the thus formed PU material. Nile Red label facilitates visualisation of copolymer in relation to the polyurethane material and to extraction washings isolated from the material.

1. Synthesis of Copolymers
1.1 Synthesis of Nile Red Acrylate (5-Diethylamino)-2-Nitrosophenol Hydrochloride 3-Diethylaminophenol (5 g) was dissolved in a mixture of concentrated HCl (11 ml) and water (6 ml) and cooled on ice. A solution of sodium nitrite (2.1 g) in water (35 ml) was added dropwise over 1 hour and the resulting slurry stirred on ice for a further 2 hours. The crude product was dissolved in boiling ethanol and recrystallized with diethyl ether to yield a yellow/orange solid (3.7 g, 50% yield). Mass spectrometry found m/z=195, expected 195.

9-Diethylamino-2-hydroxy-5H-benzo[R]phenoxazin-5-one Hydroxy Nile Red

5-Diethylamino-2-nitrosophenol hydrochloride (1.5 g) and 1,6-dihydroxynaphthalene (1.05 g) were dissolved in DMF (180 ml) and refluxed for 7 hours. The solvent was removed and the residue purified by silica gel column chromatography (petroleum spirit:ethyl acetate 20%-100%) yielding 0.52 g (20%) of a dark blue solid. $^1$H NMR in DMSO d6: ☐=10.4 (1H, s), 7.95 (1H, d), 7.88 (1H, d), 7.6 (1H, d), 7.08 (1H, d), 6.8 (1H, d), 6.6 (1H, d), 6.15 (1H, s), 3.5 (4H, q), 1.18 (6H, t). Mass spectrometry found m/z=335, expected 335.

Nile Red Acrylate

Hydroxy nile (0.5 g) was dissolved in dichloromethane (140 ml) and triethylamine (870 ml) and acryloyl chloride (500 ml) added. The solution was stirred at room temperature for 7 hours. Solvent was removed and the residue purified by silica gel column chromatography (petroleum spirit:ethyl acetate (2:1) yielding 0.2 g (34%). $^1$H NMR in DMSO d6: □=8.3 (1H, d), 8.2 (1H, d), 7.6 (1H, d), 7.5 (1H, d), 6.85 (1H, d), 6.75 (1H, d), 6.6 (1H, d), 6.5 (1H, q), 6.3 (1H, s), 6.2 (1H, d), 3.5 (4H, q), 1.2 (6H, t). mass spectrometry found m/z=389, expected 389.

1.2 Hydrophilic Copolymers

NIPAM-Nile Red Copolymer

The copolymer with n-isopropyl acrylamide was prepared using n-isopropyl acrylamide.

EPAM-Nile Red Copolymer

The copolymer with ethyl acrylamide monomer was prepared using ethyl acrylamide.

1.3 Variant Dyes

The corresponding copolymer with Dansyl was prepared by analogy using dansyl acrylamide in place of nile red acrylate.

Example 2 Immobilisation of Synthesised Copolymers in Polyurethane Material

Generation of pH Responsive PU Foam

Materials

Hydrophilic copolymer (polyacrylic acid-co-acrylamide-co-Nile Red,
methacrylic acid-co-acrylamide-co-Nile Red or
vinylsulphonic acid-co-acrylamide-co-Nile red)
Hypol 2002 (isocyanate solution): Batch no 21.8.12 (Smith & Nephew)
Brij solution: Batch no 21.8.12 (Smith & Nephew)
THF: Batch no STBD2989V (Sigma)
Method Step 1. Hypol 2002 (batch no. 21.8.1, stored at 38 C, 10 g) is weighed into a small 60 ml plastic container and hydrophilic copolymer (0.5 g, powder or dissolved in THF 5 ml) is added and mixed thoroughly, and then placed in the incubator for approximately 5 minutes.

Step 2. The aqueous phase (Brij solution) is weighed (8.5 g) into a small 60 ml plastic pot.

Step 3. The Hypol/polymer mix is removed from the incubator and the aqueous phase immediately added, and the mixture stirred rapidly with a spatula, until the two phases had created a creamy emulsion (approximately 10-15 seconds).

Step 4. The emulsion is poured into a clean 60 ml container and allowed to foam.

Step 5. After approximately 15 minutes once the foam has cured to a non-tacky elastomeric foam, it is removed from the container and dried at 40-50 C overnight in a vacuum oven set at 20 mbar.

Generation of pH Responsive PU Film

Materials
Hydrophilic copolymer (above)
Hypol 2002 (isocyanate solution): Batch no 857370 (Smith & Nephew)
THF (Sigma Aldrich Batch no STBB0055H9)
Tin octoate Sigma Aldrich Batch no SLBC8056V
Butane diol Sigma Aldrich Batch no STBF1852V 2.2.1 Method Step 1. Hypol (5 g) heated to 40 C for ease of handling and tin octoate (0.5 ml) are dissolved in THF (40 ml). Butane diol (0.227 g) in THF (10 ml) is added and the solution refluxed for 5 hours.

Step 2. Hydrophilic copolymer (0.5 g, dissolved in water/THF (1 ml/2 ml) is added to the HYPOL/butane diol solution and refluxed for a further hour.

Step 3. The Hypol/copolymer solution is allowed to cool.

Step 4. The cooled Hypol/copolymer solution is poured onto siliconized release paper.

Step 5. Solvent is allowed to evaporate. The resulting film is washed using established procedure.

2.2.1 Results

A pink colored film is obtained. Further extraction produces clear washings indicating that hydrophilic copolymer is successfully immobilised in the film.

Generation of pH Responsive PU Xerogel Adhesive

Materials

As 2.2 above 2.3.1 Method

Step Pre 1. Generation of Prepolymer: A polyoxyethylene-polyoxypropyeneddmonobuty ether, which has a ratio of polyoxyethylene to polyoxypropylene residues of 1:1 and molecular weight of 4095{300 g, 0.073 moles based on OH value) and a polymericmethylenediphenyldiisocyanate (3721 g, 0.266 moles, —NCO functionality of 2.7) are mixed together at an NCO/OH ratio of 2.5 in a700 cm$^3$ flangeflask fitted with anoverheadstirrer.

The flask is heated in a water bath set to a temperature of 90° C.

A catalyst comprising dibutyltindilaurate{0.2% w/w) is added. The mixture is stirred at 90° C. for two hours The prepolymer so formed is allowed to cool. The prepolymer is a golden yellow viscous liquid which may be stored in a capped bottle until ready for use.

The prepolymer is found to have an isocyanate content of 1.98%.

Step 1. Hydrophilic copolymer is dissolved in PU prepolymer from Step Pre 1, used in place of HYPOL of Method 2.1.1.

Steps 2-3 of Method 2.1.1 and Steps 4-5 of Method 2.2.1 are followed with the following adaptation:

Step 2 of Method 2.1.1. A glycol used in place of the Brij solution. A portion of the prepolymer and the calculated quantity of glycol which would react with all the available isocyanate a remixed at room temperature until homogeneous.

Step 3 as Method 2.1.1.

Step 4 as Method 2.2.1. The prepolymer hydrophilic copolymer diethyleneglycol then spread onto a silicone release paper at a weight per unit are a of 280 gsm and cured at 90° C. to give an adhesive mass.

Step 5 as Method 2.2.1. The adhesive mass contains 85% by weight of water when fully hydrated.

A precast film of a thermoplastic polyether polyurethane maybe transfer coated onto the adhesive mass. and the laminate strip so formed cut into pieces which are suitable for adhesive dressings and packed in a bacteria proof and water proof package and sterilised by irradiation.

2.3.2 Method

Step 1 as Method 2.3.1 except that polyoxyethylene/polyoxyproylene glycol is reacted with Desmodur N100, a solvent free aliphatic polyisocyanate, essentially 3 functional, in a molar ratio of 2:1 to form a prepolymer.

Example 3. Immobilisation and Extraction Studies; Hydrophilic Response and Sterilisation Aim:

This example shows the immobilisation of branched polymer in the polyurethane network. The hydrophobic response of the immobilised branched polymer was maintained as evidenced by change in Nile red coloration in different solutions. 5 washings were found to be effective in removing residual non-bound polymer. UV and compiled peak wavelengths of aqueous EtOH and pure EtOH washings of HBPNIPAM polymers immobilised in foam (eg ALLEVYN foam) were analysed.

Example 3.1/Solvent Extraction Aqueous Ethanol

Three copolymers produced by the above methodology are incorporated into foam during the foaming process. These foams are then washed and the washing solution analysed to determine if any of the copolymers has leached out of the foam. The foams are also tested in different hydrophilic environments to determine the effect of hydrophobicity on the foams.

Samples
Hydrophilic copolymer (polyacrylic acid-co-acrylamide-co-Nile Red,
methacrylic acid-co-acrylamide-co-Nile Red or
vinylsulphonic acid-co-acrylamide-co-Nile red)
Aqueous/Ethanolic Extracts of Polymer Foams
1. Samples of each of the foams (0.5 g) were placed in plastic containers (60 ml) and 5% aqueous ethanol (20 ml) added
2. The mixture was agitated using an orbital shaker and left for 2 hours
3. The foams were removed from the liquid and squeezed to release as much solution as possible
4. The extracted solution were then tested using UV spectral analysis, the following samples were analysed Control foam was made and washed in addition to the polymer foams. The UV spectra of the washes from the control foam gave an indication of any residues that are washed out of standard foams, and can be used to determine any differences seen with the polymer foams wash spectra. Spectra for the control foam had a peak with a maxima between 284.49 nm and 285.48 nm, hence for any foam that was washed in these conditions a peak in or close to this region would be expected.

Results Hydrophobic and Hydrophilic Response of Nile Red Polymer and Nile Red Polymer Foam The Nile red polymer sample 3.1.1 was placed in deionised water and THF to give the two different environments for the polymer to respond the hydrophobicity. The Nile red in the water responded by having a purple/pink colouration and the Nile red in the THF gave a pink/orange slightly fluorescent solution. This indicates that the Nile red still reacts to changes in the degree of hydrophobicity while co-polymerised with NIPAM. The polymer was also put into ethanol and acetone to show the colour spectrum in different degrees of hydrophobicity, with ethanol being the least hydrophobic and THF being the most hydrophobic environment. This can be seen in FIG. 2.3 (a).

The foam 3.1.1 was placed in both water and THF and an image of these pieces of foam can be seen in FIG. 2.3 (b). The foam in water has a purple/blue colour and the foam in the THF has a pink/orange colour, showing that the Nile red polymer is still reactive to different hydrophobicity environments when incorporated/immobilised into the foam.

Example 4.1 Fluorescence Detection of Polymer in PU Foam Using LED Powered Device Images of foam were taken using a fluorescence excitation and imaging device (Excitation with a 580 nm LED array and emission measured with a 647±5 nm band pass filter).

4.2.1 Thermal Response of Polymer
Aim
To investigate the fluorescent properties of P-NIPAM/van nile red polymers when made into a polyurethane foam or film dressing.
Materials
25:1 P-NIPAM/van/NR (4% wt polymer in PU foam prepared by the method of Example 2.1.1
Methods
Images were taken of foam dressings at various temperatures and post washing 5× with 5% aqueous ethanol.
Results
25:1 P-NIPAM/van nile red polymer in polyurethane foam was incubated at 4° C., room temperature, and 50° C. alongside polyurethane foam without polymer (Control). The foam was then imaged using the excitation and imaging device and an increase in fluorescence saturation (blue pixels) could be clearly seen when increasing temperature. This result suggested that the polymer was still capable of undergoing a thermoresponsive coil-to-50 globule transition
Results are shown in FIG. 2.2

Example 4.2 Fluorescent Activity of Dressing Comprising Polymer in PU Foam Supported on Adhesive Film Aim
To investigate the ability to detect fluorescence of P-NIPAM/van/nile red polymers when made into a polyurethane foam dressing.
Materials
Island Dressing comprising 25:1 P-NIPAM/van/NR in PU foam (prepared by the method of Example 2.1.1) supported on OPSITE adhesive film
Methods
The material was imaged
Results
The results in FIG. 2.2 show excellent imaging of fluorescence of the material.

The invention claimed is:
1. A device for indicating pH at a locus in the range pH 5 to pH 10, comprising a surface configured to contact the locus, wherein the device comprises polyurethane material distributed in relation to said surface, which polyurethane material comprises:
a polyurethane network having immobilised therein a hydrophilic copolymer, the hydrophilic copolymer comprising:
a hydrophilic monomer comprising an acrylol group; and
an ionisable group or moiety provided on the hydrophilic copolymer, the ionisable group or moiety having a characteristic pKa value in the range 2 to 12;
wherein a hydrophilic state of the hydrophilic copolymer is affected by ionisation of the ionisable group or moiety; and
wherein the hydrophilic copolymer further comprises an indicator monomer which provides indication of a hydrophilic state of the hydrophilic copolymer, the hydrophilic state responsive to changes in pH present at the locus.

2. The device of claim 1, further comprising an opposing non-locus contacting surface, wherein either surface or both comprises the polyurethane material distributed in relation to said surface.

3. The device of claim 2, wherein either surface or both provides a pH indicating zone comprising the polyurethane material.

4. The device of claim 1, wherein the surface comprises the polyurethane material or the polyurethane material is applied to the locus contacting surface, and wherein the surface may comprise polyurethane material at a face thereof configured to contact the locus or at an opposing face thereof.

5. The device of claim 1, wherein the surface and/or the polyurethane material is fluid permeable.

6. The device of claim 1, wherein the hydrophilic monomer comprises acrylamide, acrylate, or acrylic acid.

7. The device of claim 1, wherein the ionisable group comprises acid, acrylic acid, methacrylic acid, or sulphonic acid.

8. The device of claim 1, wherein the indicator monomer comprises solvatochromic dyes or colour changing indicators.

9. The device of claim 1, wherein the device is configured for medical, dental, hygiene, point of use sterilisation, sanitation, personal care, biosurveillance or packaging use.

10. The device of claim 1, wherein the device is configured for inspection or scanning or reading with the use of an inspection or scanning device or reader configured to receive information relating to the indication or a change in indication and provide output information relating to pH present at the locus, with use of a device comprising interrogation means for acquiring the indicating information;

a processor for processing the indicating information and generating the output information, and a display or connectivity for a display for displaying the output information.

11. A kit comprising the device of claim 10, the kit further comprising a reference strip providing reference information for processing the information relating to indication and change in indication and generating indicating information.

* * * * *

UNITED STATES PATENT AND TRADEMARK OFFICE
CERTIFICATE OF CORRECTION

| | |
|---|---|
| PATENT NO. | : 11,471,076 B2 |
| APPLICATION NO. | : 16/070260 |
| DATED | : October 18, 2022 |
| INVENTOR(S) | : John Kenneth Hicks |

It is certified that error appears in the above-identified patent and that said Letters Patent is hereby corrected as shown below:

On the Title Page

Column 2 (Item (56) Other Publications), Line 1, delete "Areview," and insert -- A review, --.

Page 2, Column 1 (Item (57) Abstract), Line 3-7, delete "and in that hydrophilic state of hydrophilic copolymer is dependent on ionisation of said ionisable groups, moieties or monomers; kit and device comprising the material and process for preparation thereof; and use in detecting or sensing microbes or pH." and insert the same on page 2, Column 1, Line 2 of Abstract, as continuation of the same paragraph.

Page 3, Column 2 (Item (56) Other Publications), Line 18, delete "Reporton" and insert -- Report on --.

Page 3, Column 2 (Item (56) Other Publications), Line 37, delete "Amercial" and insert -- American --.

Page 3, Column 2 (Item (56) Other Publications), Line 50, delete ""Luminiscent" and insert -- "Luminescent --.

In the Drawings

Sheet 1 of 5 (Figure 1), Line 12 (approx.), and on the title page, the illustrative figure, delete "Brij72/ prepared" and insert -- Brij72/prepared --.

Sheet 1 of 5 (Figure 1), Line 18 (approx.), and on the title page, the illustrative figure, delete "copolymer /PU" and insert -- copolymer/PU --.

In the Specification

Column 1, Line 13, delete "DEVICES"" and insert -- DEVICES". --.

Signed and Sealed this
Eleventh Day of April, 2023

Katherine Kelly Vidal
*Director of the United States Patent and Trademark Office*

CERTIFICATE OF CORRECTION (continued)
U.S. Pat. No. 11,471,076 B2

Column 4, Line 18, delete "pH5" and insert -- pH 5 --.

Column 4, Line 26, delete "pH10." and insert -- pH 10. --.

Column 7, Line 6, delete "bacteria or" and insert -- bacterial or --.

Column 9, Line 16, delete "contact" and insert -- contact. --.

Column 9, Line 44, delete "copolymer" and insert -- copolymer. --.

Column 10, Line 27, delete "did" and insert -- diol --.

Column 10, Line 31, delete "did" and insert -- diol --.

Column 10, Line 43, delete "did" and insert -- diol --.

Column 10, Line 49, delete "did" and insert -- diol --.

Column 10, Line 55, delete "did" and insert -- diol --.

Column 12, Line 31 (approx.), delete "COOH" and insert -- —COOH --.

Column 12, Line 64, delete "(GMA" and insert -- (GMA) --.

Column 13, Line 1, delete "methacroyloyl" and insert -- methacryloyl --.

Column 13, Line 3, delete "(HPMA)" and insert -- (HPMA). --.

Column 13, Line 31, delete "polyvinyl" and insert -- poly(vinyl --.

Column 14, Line 15-19 (approx.), delete " " and insert -- --. 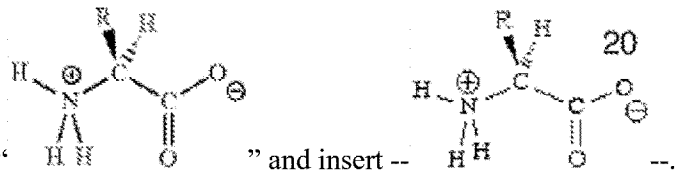

Column 14, Line 23 (approx.), After "of" insert -- the common amino acids except glycine are chiral (have a --.

Column 13-14, Line 42 (approx.), delete "CH$_2$CH(CH$_3$)2" and insert -- CH$_2$CH(CH$_3$)$_2$ --.

Column 15-16, Line 7 (approx.), delete "(CH$_2$)4NH$_2$" and insert -- (CH$_2$)$_4$NH$_2$ --.

Column 15, Line 34, delete "lysine" and insert -- Lysine --.

Column 15, Line 38, delete "□" and insert -- α, --.

CERTIFICATE OF CORRECTION (continued)
U.S. Pat. No. 11,471,076 B2

Column 15, Line 39, delete "□" and insert -- α, --.

Column 15, Line 57, delete "moieties," and insert -- moieties. --.

Column 17, Line 28, delete "cadavarine" and insert -- cadaverine --.

Column 17, Line 36, delete "(diethylamino(benzo" and insert -- (diethylamino)benzo --.

Column 17, Line 41, delete "12" and insert -- (2 --.

Column 17, Line 43, delete "12" and insert -- (2 --.

Column 17, Line 47, delete "16" and insert -- (6 --.

Column 18, Line 7, delete "215" and insert -- 215. --.

Column 18, Line 10, delete "thecorresponding" and insert -- the corresponding --.

Column 18, Line 15, delete "nm," and insert -- nm. --.

Column 18, Line 18, delete "cadavarine" and insert -- cadaverine --.

Column 19, Line 3, delete "monomer" and insert -- monomer. --.

Column 19, Line 38, delete "(oxacilin" and insert -- (oxacillin --.

Column 19, Line 40, delete "Aspergillis braziliansis." and insert -- Aspergillus brasiliensis. --.

Column 20, Line 33, delete "dressing" and insert -- dressing. --.

Column 23, Line 24, delete "(MOlnlycke" and insert -- (Mölnlycke --.

Column 23, Line 39, after "wound" delete "50".

Column 24, Line 6, delete "FIG." and insert -- FIGS. --.

Column 26, Line 26, after "combination" delete "50".

Column 27, Line 21, delete "and or" and insert -- and/or --.

Column 27, Line 45, delete "pH8" and insert -- pH 8 --.

Column 30, Line 13 (approx.), delete "OH→[prepoly" and insert -- OH→*[prepoly --.

Column 30, Line 14 (approx.), delete "(I)→$^x$poly" and insert -- (I)→*$^x$poly --.

CERTIFICATE OF CORRECTION (continued)
U.S. Pat. No. 11,471,076 B2

Column 30, Line 15 (approx.), delete "R¹co" and insert -- $R^1$ co --.

Column 30, Line 15 (approx.), delete "copoly(I)" and insert -- copoly (I) --.

Column 31, Line 59, delete "(MA-L-ALaOMe)" and insert -- (MA-L-AlaOMe) --.

Column 33, Line 6, delete "chloromatography" and insert -- chromatography --.

Column 34, Line 24, delete "polyoxypropyeneddmonobuty" and insert -- polyoxypropylene diol monobutyl --.

Column 34, Line 26, delete "4095{300" and insert -- 4095 (300 --.

Column 34, Line 29, delete "a700" and insert -- a 700 --.

Column 34, Line 30 (approx.), delete "flangeflask" and insert -- flange flask --.

Column 34, Line 30 (approx.), delete "anoverheadstirrer." and insert -- an overhead stirrer. --.

Column 34, Line 33 (approx.), delete "dibutyltindilaurate{0.2%" and insert -- dibutyltindilaurate (0.2% --.

Column 34, Line 34 (approx.), delete "hours" and insert -- hours. --.

Column 34, Line 49, delete "a remixed" and insert -- are mixed --.

Column 34, Line 54, delete "are a" and insert -- area --.

Column 34, Line 59, delete "maybe" and insert -- may be --.

Column 34, Line 59, delete "mass." and insert -- mass --.

Column 34, Line 65, delete "polyoxyproylene" and insert -- polyoxypropylene --.

Column 35, Line 40, delete "analysed" and insert -- analysed. --.

Column 36, Line 18, delete "2.1.1" and insert -- 2.1.1. --.

Column 36, Line 30, delete "coil-to-50 globule" and insert -- coil-to-globule --.

Column 36, Line 30, delete "transition" and insert -- transition. --.

Column 36, Line 31, delete "2.2" and insert -- 2.2. --.

Column 36, Line 44 (approx.), delete "film" and insert -- film. --.

CERTIFICATE OF CORRECTION (continued)
U.S. Pat. No. 11,471,076 B2

Column 36, Line 46 (approx.), delete "imaged" and insert -- imaged. --.

In the Claims

Column 36, Line 59, In Claim 1, delete "acrylol" and insert -- acryloyl --.

Column 38, Line 10, In Claim 10, after "change in" insert -- the --.